US009669086B2

(12) United States Patent
Roof et al.

(10) Patent No.: US 9,669,086 B2
(45) **Date of Patent: *Jun. 6, 2017**

(54) **PCV2 *MYCOPLASMA HYOPNEUMONIAE* IMMUNOGENIC COMPOSITIONS AND METHODS OF PRODUCING SUCH COMPOSITIONS**

(71) Applicant: Boehringer Ingelheim Vetmedica, Inc., St. Joseph, MO (US)

(72) Inventors: Michael Roof, Ames, IA (US); Marc Eichmeyer, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/641,691

(22) Filed: Mar. 9, 2015

(65) Prior Publication Data

US 2015/0174233 A1 Jun. 25, 2015

Related U.S. Application Data

(63) Continuation of application No. 12/359,023, filed on Jan. 23, 2009, now abandoned.

(60) Provisional application No. 61/023,086, filed on Jan. 23, 2008, provisional application No. 61/025,293, filed on Jan. 31, 2008.

(51) Int. Cl.

| | |
|---|---|
| ***A61K 39/12*** | (2006.01) |
| ***A61K 39/02*** | (2006.01) |
| ***A61K 39/39*** | (2006.01) |
| ***C12N 7/00*** | (2006.01) |
| *A61K 39/00* | (2006.01) |

(52) U.S. Cl.

CPC .......... *A61K 39/12* (2013.01); *A61K 39/0208* (2013.01); *A61K 39/0241* (2013.01); *A61K 39/39* (2013.01); *C12N 7/00* (2013.01); *A61K 2039/525* (2013.01); *A61K 2039/545* (2013.01); *A61K 2039/552* (2013.01); *A61K 2039/55555* (2013.01); *A61K 2039/70* (2013.01); *C12N 2750/10034* (2013.01); *C12N 2750/10071* (2013.01)

(58) Field of Classification Search

None

See application file for complete search history.

(56) References Cited

U.S. PATENT DOCUMENTS

| | | | |
|---|---|---|---|
| 5,026,543 | A | 6/1991 | Rijke |
| 5,155,037 | A | 10/1992 | Summers |
| 5,202,430 | A | 4/1993 | Brian et al. |
| 5,322,774 | A | 6/1994 | Peakman et al. |
| 5,436,001 | A | 7/1995 | Kramer |
| 5,565,205 | A | 10/1996 | Petersen et al. |
| 5,580,557 | A | 12/1996 | Kramer |
| 5,733,555 | A | 3/1998 | Chu |
| 5,885,823 | A | 3/1999 | Knittel et al. |
| 5,925,359 | A | 7/1999 | Van Woensel et al. |
| 5,968,525 | A | 10/1999 | Fitzgerald et al. |
| 6,217,883 | B1 | 4/2001 | Allan et al. |
| 6,287,856 | B1 | 9/2001 | Poet et al. |
| 6,294,176 | B1 | 9/2001 | Cochran et al. |
| 6,368,601 | B1 | 4/2002 | Allan et al. |
| 6,391,314 | B1 | 5/2002 | Allan et al. |
| 6,497,883 | B1 | 12/2002 | Bublot et al. |
| 6,517,843 | B1 | 2/2003 | Ellis et al. |
| 6,660,272 | B2 | 12/2003 | Allan et al. |
| 6,703,023 | B1 | 3/2004 | Jestin et al. |
| 6,794,163 | B2 | 9/2004 | Liu et al. |
| 6,808,900 | B2 | 10/2004 | Simonsen |
| 6,841,364 | B2 | 1/2005 | Yuan et al. |
| 6,846,477 | B2 | 1/2005 | Keich et al. |
| 6,943,152 | B1 | 9/2005 | Audonnet et al. |
| 6,953,581 | B2 | 10/2005 | Allan et al. |
| 7,018,638 | B2 | 3/2006 | Chu et al. |
| 7,109,025 | B1 | 9/2006 | Eloit et al. |
| 7,122,192 | B2 | 10/2006 | Allan et al. |
| 7,144,698 | B2 | 12/2006 | Wang et al. |
| 7,148,015 | B2 | 12/2006 | Jestin et al. |
| 7,169,394 | B2 | 1/2007 | Chu et al. |
| 7,172,899 | B2 | 2/2007 | Liu et al. |
| 7,179,472 | B2 | 2/2007 | Jestin et al. |
| 7,192,594 | B2 | 3/2007 | Haines et al. |

(Continued)

FOREIGN PATENT DOCUMENTS

| | | | |
|---|---|---|---|
| CA | 2264953 | A1 | 2/1998 |
| CA | 2305623 | A1 | 4/1999 |

(Continued)

OTHER PUBLICATIONS

Ladekjaer-Mikkelsen et al., "Reproduction of postweaning multisystemic wasting syndrome (PMWS) in immunostimulated and non-immunostimulated 3-week-old piglets experimentally infected with prcine circovirus type 2 (PCV2)". 2002, Veterinary Microbiology, vol. 89, pp. 97-114.

Lekcharoensuk et al., "Epitope Mapping of the Major Capsid Protein of Type 2 Porcine Circovirus (PCV2) by Using Chimeric PCV1 and PCV2". Journal of Virology, vol. 78, No. 15, Aug. 2004, pp. 8135-8145.

Li et al., "Expression and Self-Assembly of Empty Virus-Like Particle of Hepatitis E Virus". Journal of Virology, vol. 71, No. 10, Oct. 1997, pp. 7207-7213.

Lin et al., "Mycoplasma hyorhinis in Taiwan: Diagnosis and isolation of swine pneumonia pathogen". Veterinary Microbiology, vol. 115, 2006, pp. 111-116.

(Continued)

*Primary Examiner* — Brian J Gangle

(74) *Attorney, Agent, or Firm* — Michael P. Morris; Wendy M. Gombert

(57) ABSTRACT

Multivalent combination vaccines are provided which include an immunological agent effective for reducing the incidence of or lessening the severity of *M. hyo* infection, preferably *M. hyo* bacterin, or an immunogenic composition comprising *M. hyo* bacterin, and at least one immunogenic active component of another disease-causing organism in swine, preferably PCV2 wherein the preferred PCV2 antigen for such a multivalent vaccine is PCV2 ORF 2 protein.

11 Claims, No Drawings

(56) References Cited

U.S. PATENT DOCUMENTS

| | | | |
|---|---|---|---|
| 7,211,379 | B2 | 5/2007 | Ellis et al. |
| 7,223,407 | B2 | 5/2007 | Jestin et al. |
| 7,223,594 | B2 | 5/2007 | Jestin et al. |
| 7,244,433 | B2 | 7/2007 | Jestin et al. |
| 7,258,865 | B2 | 8/2007 | Jestin et al. |
| 7,261,898 | B2 | 8/2007 | Jestin et al. |
| 7,273,617 | B2 | 9/2007 | Yuan et al. |
| 7,276,353 | B2 | 10/2007 | Meng et al. |
| 7,279,166 | B2 | 10/2007 | Meng et al. |
| 7,297,537 | B2 | 11/2007 | Jestin et al. |
| 7,300,785 | B2 | 11/2007 | Meerts et al. |
| 7,312,065 | B2 | 12/2007 | Roof et al. |
| 7,314,628 | B2 | 1/2008 | Jestin et al. |
| 7,323,330 | B2 | 1/2008 | Jestin et al. |
| 7,335,361 | B2 | 2/2008 | Liao et al. |
| 7,358,075 | B2 | 4/2008 | Allibert et al. |
| 7,368,117 | B2 | 5/2008 | Fetzer et al. |
| 7,371,395 | B2 | 5/2008 | Parisot et al. |
| 7,390,494 | B2 | 6/2008 | Jestin et al. |
| 7,405,075 | B2 | 7/2008 | Jestin et al. |
| 7,407,803 | B2 | 8/2008 | Jestin et al. |
| 7,425,444 | B2 | 9/2008 | Jestin et al. |
| 7,700,285 | B1 | 4/2010 | Eichmeyer et al. |
| 7,758,865 | B2 | 7/2010 | Jestin et al. |
| 7,829,101 | B2 | 11/2010 | Eichmeyer et al. |
| 7,829,273 | B2 | 11/2010 | Roof et al. |
| 7,829,274 | B2 | 11/2010 | Fachinger et al. |
| 7,833,707 | B2 | 11/2010 | Eichmeyer et al. |
| 7,838,213 | B2 | 11/2010 | Roof et al. |
| 7,838,214 | B2 | 11/2010 | Roof et al. |
| 7,910,306 | B2 | 3/2011 | Eichmeyer et al. |
| 7,914,992 | B2 | 3/2011 | Fachinger et al. |
| 7,943,298 | B2 | 5/2011 | Fachinger et al. |
| 7,951,907 | B2 | 5/2011 | Jestin et al. |
| 7,968,285 | B2 | 6/2011 | Roof et al. |
| 8,025,888 | B2 | 9/2011 | Eichmeyer et al. |
| 8,119,143 | B2 | 2/2012 | Roof et al. |
| 8,475,805 | B2 | 7/2013 | Fachinger et al. |
| 8,496,940 | B2 | 7/2013 | Fachinger et al. |
| 8,852,613 | B2 | 10/2014 | Ohnesorge et al. |
| 8,865,183 | B2 | 10/2014 | Fachinger et al. |
| 9,011,868 | B2 | 4/2015 | Roof et al. |
| 9,011,872 | B2 | 4/2015 | Eichmeyer et al. |
| 2002/0146431 | A1 | 10/2002 | Allan et al. |
| 2003/0096377 | A1 | 5/2003 | Meng et al. |
| 2003/0170270 | A1 | 9/2003 | Meng et al. |
| 2003/0199581 | A1 | 10/2003 | Seligson et al. |
| 2003/0215455 | A1 | 11/2003 | Reynolds et al. |
| 2004/0062775 | A1 | 4/2004 | Jestin et al. |
| 2004/0076635 | A1 | 4/2004 | Jestin et al. |
| 2004/0091502 | A1 | 5/2004 | Jestin et al. |
| 2004/0132178 | A1 | 7/2004 | Haines et al. |
| 2004/0161410 | A1 | 8/2004 | Jestin et al. |
| 2004/0208901 | A1 | 10/2004 | Ellsworth et al. |
| 2004/0253270 | A1 | 12/2004 | Meng et al. |
| 2004/0258715 | A1 | 12/2004 | Allan et al. |
| 2004/0265848 | A1 | 12/2004 | Jestin et al. |
| 2005/0008651 | A1 | 1/2005 | Jestin et al. |
| 2005/0013823 | A1 | 1/2005 | Keich et al. |
| 2005/0031647 | A1 | 2/2005 | Roof et al. |
| 2005/0058653 | A1 | 3/2005 | Ellis et al. |
| 2005/0079185 | A1 | 4/2005 | Parisot et al. |
| 2005/0084497 | A1 | 4/2005 | Jestin et al. |
| 2005/0147966 | A1 | 7/2005 | Meng et al. |
| 2005/0238662 | A1 | 10/2005 | Jestin et al. |
| 2006/0002952 | A1 | 1/2006 | Haines et al. |
| 2006/0029617 | A1 | 2/2006 | Charreyre et al. |
| 2006/0083756 | A1 | 4/2006 | Jestin et al. |
| 2006/0115489 | A1 | 6/2006 | Birkett et al. |
| 2006/0204522 | A1 | 9/2006 | Kroll et al. |
| 2006/0222659 | A1 | 10/2006 | Jestin et al. |
| 2006/0228373 | A1 | 10/2006 | Chu et al. |
| 2006/0233831 | A1 | 10/2006 | Parisot et al. |
| 2006/0246425 | A1 | 11/2006 | Allibert et al. |
| 2006/0286123 | A1 | 12/2006 | Fetzer et al. |
| 2007/0196879 | A1 | 8/2007 | Chabriere et al. |
| 2008/0181910 | A1 | 7/2008 | Roof et al. |
| 2008/0226669 | A1 | 9/2008 | Roof et al. |
| 2008/0233147 | A1 | 9/2008 | Jestin et al. |
| 2008/0261887 | A1 | 10/2008 | Roof et al. |
| 2008/0267995 | A1 | 10/2008 | Roof et al. |
| 2008/0279875 | A1 | 11/2008 | Roof et al. |
| 2008/0279876 | A1 | 11/2008 | Roof et al. |
| 2008/0279889 | A1 | 11/2008 | Roof et al. |
| 2009/0016992 | A1 | 1/2009 | Eichmeyer et al. |
| 2009/0017064 | A1 | 1/2009 | Wu et al. |
| 2009/0022751 | A1 | 1/2009 | Eichmeyer et al. |
| 2009/0042245 | A1 | 2/2009 | Eichmeyer et al. |
| 2009/0317423 | A1 | 12/2009 | Roof et al. |
| 2010/0136060 | A1 | 6/2010 | Kolb |
| 2010/0184016 | A1 | 7/2010 | Lefebvre et al. |
| 2010/0189743 | A1 | 7/2010 | Jestin et al. |
| 2011/0033495 | A1 | 2/2011 | Roof et al. |
| 2011/0059126 | A1 | 3/2011 | Kohler et al. |
| 2011/0091499 | A1 | 4/2011 | Fachinger et al. |
| 2011/0217327 | A1 | 9/2011 | Roof et al. |
| 2011/0274710 | A1 | 11/2011 | Eichmeyer et al. |
| 2013/0115236 | A1 | 5/2013 | Fachinger et al. |
| 2013/0230558 | A1 | 9/2013 | Ohnesorge et al. |
| 2013/0273099 | A1 | 10/2013 | Fachinger et al. |
| 2013/0302370 | A1 | 11/2013 | Fachinger et al. |
| 2014/0322267 | A1 | 10/2014 | Haiwick et al. |
| 2014/0348874 | A1 | 11/2014 | Segales et al. |
| 2014/0377298 | A1 | 12/2014 | Fachinger et al. |
| 2015/0056248 | A1 | 2/2015 | Haiwick et al. |
| 2015/0093404 | A1 | 4/2015 | Hernandez et al. |
| 2015/0297707 | A1 | 10/2015 | Roof et al. |
| 2015/0297708 | A1 | 10/2015 | Roof et al. |

FOREIGN PATENT DOCUMENTS

| | | | |
|---|---|---|---|
| CN | 1579553 | A | 7/1920 |
| CN | 1458167 | A | 11/2003 |
| CN | 103122352 | A | 5/2013 |
| EP | 1050584 | A1 | 11/2000 |
| EP | 1281760 | A1 | 2/2003 |
| EP | 1386617 | A1 | 2/2004 |
| JP | 2002247979 | A | 9/2002 |
| JP | 2005511075 | A | 4/2005 |
| WO | 8906972 | A1 | 8/1989 |
| WO | 9007935 | A1 | 7/1990 |
| WO | 9118627 | A1 | 12/1991 |
| WO | 9203157 | A1 | 3/1992 |
| WO | 9316726 | A2 | 9/1993 |
| WO | 9636356 | A1 | 11/1996 |
| WO | 9918214 | A1 | 4/1999 |
| WO | 9929717 | A3 | 6/1999 |
| WO | 9929871 | A3 | 6/1999 |
| WO | 0001409 | A2 | 1/2000 |
| WO | 0047756 | A1 | 8/2000 |
| WO | 0077188 | A2 | 12/2000 |
| WO | 0077216 | A2 | 12/2000 |
| WO | 0116330 | A2 | 3/2001 |
| WO | 0117556 | A1 | 3/2001 |
| WO | 0134191 | A1 | 5/2001 |
| WO | 0145735 | A2 | 6/2001 |
| WO | 0196377 | A2 | 12/2001 |
| WO | 0249666 | A2 | 6/2002 |
| WO | 02077210 | A2 | 10/2002 |
| WO | 03003941 | A2 | 1/2003 |
| WO | 03049703 | A2 | 6/2003 |
| WO | 2004026336 | A1 | 4/2004 |
| WO | 2004058142 | A2 | 7/2004 |
| WO | 2004069184 | A2 | 8/2004 |
| WO | 2005009462 | A2 | 2/2005 |
| WO | 2005092069 | A2 | 10/2005 |
| WO | 2005112995 | A1 | 12/2005 |
| WO | 2006068663 | A2 | 6/2006 |
| WO | 2006072065 | A2 | 7/2006 |
| WO | 2006113372 | A2 | 10/2006 |
| WO | 2006113373 | A2 | 10/2006 |
| WO | 2007028823 | A1 | 3/2007 |
| WO | 2007076520 | A2 | 7/2007 |
| WO | 2007094893 | A2 | 8/2007 |

(56) References Cited

FOREIGN PATENT DOCUMENTS

| | | | |
|---|---|---|---|
| WO | 2008073464 | A2 | 6/2008 |
| WO | 2008076915 | A2 | 6/2008 |
| WO | 2008081015 | A1 | 7/2008 |
| WO | 2008098909 | A1 | 8/2008 |
| WO | 2009030684 | A2 | 3/2009 |
| WO | 2009103037 | A1 | 8/2009 |
| WO | 2009126356 | A2 | 10/2009 |
| WO | 2011116094 | A2 | 9/2011 |
| WO | 2014134561 | A2 | 9/2014 |
| WO | 2014179200 | A1 | 11/2014 |
| WO | 2015026912 | A1 | 2/2015 |
| WO | 2015051099 | A1 | 4/2015 |

OTHER PUBLICATIONS

Liu et al., "Bacterial Expression of an Immunologically Reactive PCV2 ORF2 Fusion Protein". 2001, Protein Expression and Purification, vol. 21, pp. 115-120.

Liu et al., "Characterization of a Previously Unidentified Viral Protein in Porcine Circovirus Type 2-Infected Cells and Its Role in Virus-Induced Apoptosis". Jul. 2005, Journal of Virology, vol. 79, No. 13, pp. 8262-8274.

Liu et al., "Development of an ELISA Baed on the Baculovirus-Expressed Capsid Protein of Porcine Circovirus Type 2 as Antigen". Journal of Veterinary Medical Science, vol. 66, No. 3, Mar. 2004, pp. 237-242.

MacKinnon, J.D., "Vaccination Ramification? An Objective Look at How Vaccination Might Affect Post-Weaning Multisystemic Wasting Syndrome (PMWS) and Porcine Dermatitis and Nephropathy Syndrome (PDNS)". 2003, The Pig Journal, vol. 51, pp. 36-63.

Maes et al., "Effect of vaccination against Mycoplasma hyopneumoniae in pig herds with an all-in/all-out production system". Vaccine, vol. 17, 1999, pp. 1024-1034.

Mahe et al., "Differential recognition of ORF2 protein from type 1 and type 2 porcine circoviruses and identification of immunorelevant epitopes". 2000, Journal of General virology, vol. 81, pp. 1815-1824.

Maranga et al., "Virus-Like Particle Production at Low Multiplicities of Infection With the Baculovirus Insect Cell System". Aug. 2003, Biotechnology and Bioengineering, vol. 84, No. 2, pp. 246-253.

Martelli et al., "One dose of a porcine circovirus 2 subunit vaccine induces humoral and cell-mediated immunity and protects against porcine circovirus-associated disease under field conditions". Veterinary Microbiology, vol. 149, 2011, pp. 339-351.

Mateu et al., "A Single Amino Acid substitution Affects Multiple Overlapping Epitopes in the Major Antigenic Site of Foot-and-Mouth Disease Virus of Serotype C," Journal of General Virology, vol. 71, 1990, pp. 629-637.

McKeown et al., "Effects of Porcine Circovirus Type 2 (PCV2) Maternal Antibodies on Experimental Infection of Piglets with PCV2". Clinical and Diagnostic Laboratory Immunology, vol. 12, No. 11, Nov. 2005, pp. 1347-1351.

McNeilly et al., "Evaluation of a Porcine Circovirus Type 2-Specific Antigen-Captive Enzyme-Linked Immunosorbent Assay for the Diagnosis of Postweaning Multisystemic Wasting Syndrome in Pigs: Comparison with Virus Isolation, Immunohistochemistry, and the Polymerase Chain Reaction", J. Vet Diagn. Invest, 2002, 14, pp. 106-112.

Meehan et al., "Characterization of novel circovirus DNAs associated with wasting syndromes in pigs". Journal of General Virology, vol. 79, 1998, pp. 2171-2179.

Minion et al., "Then Genome Sequence of Mycoplasma hyopneumoniae Strain 232, the Agent of Swine Mycoplasmosis". Nov. 2004, Journal of Bacteriology, vol. 186, No. 21, pp. 7123-7133.

Morales et al., "Serendipitous Discovery and X-Ray Structure of a Human Phosphate Binding Apolipoprotein". Mar. 2006, Structure, vol. 14, pp. 601-609.

Morris et al., "Characterization of Productive and Non-Productive ACMNPV Infection in Selected Insect Cell Lines", Viro. 197, 1993, pp. 339-348.

Morris et al., "Promoter Influence on Baculovirus-Mediated Gene jExpression in Permissive and Nonpermissive Insect Cell Lines", J. Virol., Dec. 1992, vol. 66, No. 12, pp. 7397-7405.

Mortola et al., "Efficient assembly and release of SARS coronavirus-like particles by a heterologous expression system". FEBS Letters, vol. 576, 2004, pp. 174-178.

Muirhead, Mike, "Sources of information on PMWS/PDNS". The Veterinary Record, vol. 150, No. 14, Apr. 6, 2002, p. 456.

Murakami et al., "Occurrence of Swine Salmonellosis in Postweaning Multisystemic Wasting Syndrome (PMWS) Affected Pigs Concurrently Infected with Porcine Reproduction and Respiratory Syndrome Virus (PRRSV)". Journal of Veterinary Medical Science, vol. 68, 2006, pp. 387-391.

Nawagitgul et al., "Open reading frame 2 of porcine circovirus type 2 encodes a major capsid protein". 2000, Journal of General Virology, vol. 81, pp. 2281-2287.

Nawagitgul et al., Modified Indirect Porcine Circovirus (PCV) Type 2-based and Recombinant Capsid Protein (ORF-2) Based Enzyme-Linked Immunosorbent Assays for Detection of Antibodies to PCV, Clinical and Diagnostic Laboratory Imunology, Ja. 2002, vol. 9, No. 1, pp. 33-40.

Neutra et al., "Optimization of protein-production by the baculovirus expression vector system in shake flasks". Applied Microbiology and Biotechnology Journal, vol. 37, No. 1, 1992, pp. 74-78.

Noad et al., "Virus-like particles as immunogens" Trends in Microbiology, vol. 11, No. 9, Sep. 2003, pp. 438-444.

O'Dea et al., "Porcine circovirus-associated disease in weaner pigs in Western Australia". Australian Veterinary Journal, vol. 89, No. 4, Apr. 2011, pp. 122-130.

Ohnesorge et al., "Efficacy Studies—Efficacy evaluation of a mixed Mycoplasma hyopneumoniae bacterin and a porcine circovirus type 2 vaccine". 2007, 1 page. [Accessed at http://www.ingelvacflex.co.uk/mycoflex/research/efficacy.php on Jul. 31, 2012].

Okuda, et al., "Experimental Reproduction of Post-Weaning Multisystemic Wasting Syndrome in Cesarean-Derived, Colostrum-Deprived Piglets Inoculated with Porcine Circovirus Type 2 (PCV2): Investigation of Quantitative PCV2 Distribution and Antibody Responses", J. Vet Diagn. Invest, 2003, 15, pp. 107-114.

Olvera et al., "Comparison of porcine circovirus type 2 load in serum quantified by a real time PCR in postweaning multisystemic wasting syndrome and porcine dermatitis and nephropathy syndrome naturally affected pigs". 2004, Journa of Virological Methods, vol. 117, pp. 75-80.

Opriessnig et al., "A commercial vaccine based on PCV2a and an experimental vaccine based on a variant mPCV2b are both effective in protecting pigs against challenge with a 2013 U.S. variant mPCV2b strain". Vaccine, vol. 32, No. 2, 2014, pp. 230-237.

Opriessnig et al., "A PCV2 vaccine based on genotype 2b is more effective than a 2a-based vaccine to protect against PCV2b or combined PCV2a/2b viremia in pigs with concurrent PCV2, PRRSV and PPV infection". Vaccine, vol. 31, 2013, pp. 487-494.

Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, 2002, pp. 11837-11844.

Opriessnig et al., "Derivation of porcine circovirus type 2-negative pigs from positive breeding herds". Journal of Swine Health and Production, vol. 12, No. 4, Jul. and Aug. 2004, pp. 186-191.

Opriessnig et al., "Differences in virulence among porcine circovirus type 2 isolates are unrelated to cluster type 2a or 2b and prior infection provides heterologous protection". Journal of General Virology, vol. 89, No. 10, 2008, pp. 2482-2491.

Opriessnig et al., "Effect of porcine circovirus type 2 (PCV2) vaccination on porcine reproductive and respiratory syndrome virus (PRRSV) and PCV2 coinfection". Veterinary Microbiology, vol. 131, 2008, pp. 103-114.

(56) References Cited

OTHER PUBLICATIONS

Opriessnig et al., "Effect of Vaccination with Selective Bacterins on Conventional Pigs Infected with Type 2 Porcine Circovirus". Veterinary Pathology, vol. 40, 2003, pp. 521-529.
Opriessnig et al., "Effects of the timing of the administration of Mycoplasma hyopneumoniae bacterin on the development of lesions associated with porcine circovirus type 2". Veterinary Record, vol. 158, No. 5, Feb. 2006, pp. 149-154.
Opriessnig et al., "Experimental Co-Infection with Porcine Circovirus Type 2 and *Salmonella typhimurium* or Lawsonia Intracellularis". Pig Progress, Jun. 2008, 1 page. [Accessed at: http://www.pigprogress.net/public/file/IPVS-oral%20presentations/Viral%20diseases/Experimental%20co-infection%20with %20PCV2%20and%20salmonella%20Typhimurium%20or %20lawsonia%20intracellularis.pdf on Mar. 17, 2010].
Opriessnig et al., "Experimental Reproduction of Postweaning Multisystemic Wasting Syndrome in Pigs by Dual Infection with Mycoplasma hyopneumoniae and Porcine Circovirus Type 2". Veterinary Pathology, vol. 41, No. 6, Nov. 2004, pp. 624-640.
Opriessnig et al., "Porcine Circovirus Type 2 Infection Decreases the Efficacy of a Modified Live Porcine Reproductive and Respiratory Syndrome Virus Vaccine", Clinical and Vaccine Immunology, Aug. 2006, vol. 13, No. 8, pp. 923-929.
Ostanello et al., "Experimental infection of 3-week-old conventional colostrum-fed pigs with porcine circovirus type 2 and porcine parvovirus". Veterinary Microbiology, vol. 108, No. 3-4, Jul. 2008, pp. 179-186.
Paterson, J.E., "Health and antimicrobial resistance". Manipulating Pig Production X, Chapter 2, Proceedings of the Tenth Biennial Conference of the Australasian Pig Science Association (Inc.) (APSA) held in Christchurch, New Zealand on Nov. 27 to 30, 2005, Werribee, Victoria, Australia: Australasian Pig Association (Inc.), pp. 21-74.
Patterson et al., "Baculovirus and Insect Cell Gene Expression: Review of Baculovirus Biotechnology". Environmental Health Perspectives, vol. 103, Nos. 7-8, Jul.-Aug. 1995, pp. 756-759.
Patterson et al., "Interlaboratory Comparison of Porcine Circovirus-2 Indirect Immunofluorescent Antibody Test and Enzyme-Linked Immunosorbent Assay Results on Experimentally Infected Pigs". Journal of Veterinary Diagnostic Investigation, vol. 23, 2011, pp. 206-212.
Poljak et al., "Spread of porcine circovirus associated disease (PCVAD) in Ontario (Canada) swine herds: Part I. Exploratory spatial analysis". BMC Veterinary Research, vol. 6, No. 59, 2010, pp. 1-15.
Poppe et al., "*Salmonella typhimurium* DT104: A virulent and drug-resistant pathogen". Canadian Veterinary Journal, vol. 39, 1998, pp. 559-565.
Quintana et al., "Clinical and pathological observations on pigs with postweaning multisystemic wasting syndrome". 2001, The Veterinary Record, vol. 149, pp. 357-361.
Ragona et al., "The Transcriptional Factor Egr-1 Is Synthesized by Baculovirus-Infected Insect Cells in an Active, DNA-Binding Form". DNA and Cell Biology, vol. 10, No. 1, 1991, pp. 61-66.
Wu et al., "Replication, Integration, and Packaging of Plasmid DNA following Cotransfection with Baculovirus Viral DNA". Journal of Virology, vol. 73, No. 7, Jul. 1999, pp. 5473-5480.
Xia et al., "Preparation of and Immunity Tests with Canine Coronavirus BEI Inactivated Vaccine". Chinese Journal of Veterinary Medicine, vol. 37, No. 3, 2001, pp. 37-38.
Yamada et al., "Evaluation of the Efficacy of Inactivated Vaccine against *Salmonella enteritidis* Infection in Chicken". Journal of the Japanese Society on Poultry Diseases, vol. 35, No. 1, 1999, pp. 13-21. (English Summary at p. 21).
Yang, "A Survey on Porcine Circovirus Type 2 Infection and Phylogenetic Analysis of its ORF2 Gene in Hangzhou, Zhejiang Province, CN," J. Zhejiang Univ. Science B, vol. 9(2), 2008, pp. 148-153.
Yuan et al., "Immunology of the porcine respiratory disease complex". Animal Science Abroad in Pigs and Poultry, No. 5, 2002, pp. 36-38.
Zhang et al., "Cytokine and chemokine mRNA expression profiles in tracheobronchial lymph nodes from pigs singularly infected or coinfected with porcine circovirus type 2 (PCV2) and Mycoplasma hyopneumoniae (MHYO)". Veterinary Immunology and Immunopathology, vol. 140, 2011, pp. 152-158.
Fan et al., "Immunogenicity of Empty Capsids of Porcine Circovirus Type 2 Produced in Insect Cells". 2007, Veterinary Research Communications, vol. 31, pp. 487-496.
Fan et al., "Preclinical study of influenza virus A M2 peptide conjugate vaccines in mice, ferrets, and rhesus monkeys". Vaccine, vol. 22, 2004, pp. 2993-3003.
Fan et al., "The Expression of Porcine Circovirus Type 2 ORF2 Gene in Insect Cells and its Character". Chinese Journal of Biotechnology, vol. 21, No. 6, Nov. 2005, pp. 975-978.
Fenaux et al., "A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Imunity Against PCV2 Infection in Pigs", J. Virol, Jun. 2004, vol. 78, No. 12, pp. 6297-6303.
Fenaux et al., "Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay to Detect and Differentiate between Infections with PCV-1 and PCV-2". Journal of Clinical Microbiology, vol. 38, No. 7, Jul. 2000, pp. 2494-2503.
Fenaux et al., "Immunogenicity and Pathogenicity of Chimeric Infectious DNA Clones of Pathogenic Porcine Circovirus Type 2 (PCV2) and Nonpathogenic PCV1 in Weanling Pigs". Journal of Virology, vol. 77, No. 20, Oct. 2003, pp. 11232-11243.
Fort et al., "Porcine circovirus type 2 (PCV2) vaccination of conventional pigs prevents viremia against PCV2 isolates of different genotypes and geographic origins". Vaccine, vol. 26, No. 8, 2008, pp. 1063-1071.
Gagrcin et al., "Complex of Swine Respiratory Diseases-Strategy of control in light of latest knowledge". Veterinarski Glasnik, vol. 58, No. 7-8, 2004, pp. 409-418. [English Abstract at p. 417.].
Genbank Accession No. AAC61738, Version AAC61738.1 GI:3661517, Sep. 29, 1998.
GenBank Accession No. AF201311, Direct Submission, submitted Feb. 23, 2000 in Mankertz et al., "Characterization of PCV-2 isolates from Spain, Germany and France", Virus Research, vol. 66, No. 1, 2000, pp. 65-77, 2 pages.
Genbank Accession# AAF87231, PCV2 ORF2 Protein, 2000.
Gizurarson, Sveinbjörn, "Clinically Relevant Vaccine-Vaccine Interactions". BioDrugs, vol. 9, No. 6, Jun. 1998, pp. 443-453.
Groner, et al., The Biology of Baculoviruses, vol. 1, Biological Properties and Moleculary Biology, 1986, Chapter 9, Specificity and Safety of Baculoviruses, pp. 177-202.
Gualandi et al., "The Ability by Different Preparations of Porcine Parvovirus to Enhance Humoral Immunity in Swine and Guinea Pigs". Microbiologica, vol. 11, No. 4, 1988, pp. 363-369.
Gualandi et al., "The Response of Pregnant Gilts Previously Given an Inactivated Preparation of Porcine Parvovirus (PPV) to Challenge Infection with a Fully Virulent PPV". Microbiologica, vol. 15, 1992, pp. 391-396.
Ha et al., "Outbreak of salmonellosis in pigs with postweaning multisystemic wasting syndrome". Veterinary Record, vol. 156, No. 18, Apr. 2005, pp. 583-584.
Haake et al., "Influence of age on the effectiveness of PCV2 vaccination in piglets with high levels of maternally derived antibodies". Veterinary Microbiology, vol. 168, 2014, pp. 272-280.
Haiwick et al., "Trivalent vaccine mixture protects against simultaneous challenge with *M. hyopneumoniae*, PCV2, and PRRS virus". Allen D. Leman Swine Conference, 2010, p. 176.
Hamel et al., "Nucleotide Sequence of Porcine Circovirus Associated with Postweaning Multisystemic Wasting Syndrome in Pigs". Journal of Virology, vol. 72, No. 6, Jun. 1998, pp. 5262-5267.

(56) References Cited

OTHER PUBLICATIONS

Harding et al., "Recognizing and diagnosing postweaning multisystemic wasting syndrome (PMWS)". Swine Health and Production, vol. 5, No. 5, 1997, pp. 201-203.
Harms et al., "Three cases of porcine respiratory disease complex associated with porcine circovirus type 2 infection". Journal of Swine Health and Production, vol. 10, No. 1, 2002, pp. 27-30.
Haruna et al., "The role of immunostimulation in the development of postweaning multisystemic wasting syndrome in pigs under field conditions". Canadian Journal of Veterinary Research, vol. 70, Oct. 2006, pp. 269-276.
Hilgers et al., "Alkyl-esters of polyacrylic acid as vaccine adjuvants". Vaccine, vol. 16, No. 16, 1998, pp. 1575-1581.
Hirai et al., "Dual infection with PCV-2 and porcine epidemic diarrhoea virus in neonatal piglets". The Veterinary Record, vol. 148, 2001, pp. 482-484.
Hoogland et al., "Effects of adjuvants on porcine circovirus type 2-associated lesions". Journal of Swine Health and Production, vol. 14, No. 3, 2006, pp. 133-139.
Huang et al., "Porcine circovirus type 2 (PCV2) infection decreases the efficacy of an attenuated classical swine fever virus (CSFV) vaccine". Veterinary Research, vol. 42, 115, 2011, pp. 1-9.
Hüser et al., "Baculovirus Vectors: Novel Mammalian Cell Gene-Delivery Vehicles and Their Applications". American Journal of Pharmacogenomics, vol. 3, No. 1, 2003, pp. 53-63.
International Search Report and Written Opinion for PCT/US2009/031847 mailed Sep. 15, 2009.
Inumaru et al., "Expression of biologically active recombinant porcinee GM-CSF by baculovirus gene expression system". 1998, Immunology and Cell Biology, vol. 76, pp. 195-201.
Invitrogen Life Technologies, "Growth and Maintenance of Insect Cell Lines". Insect Cell Lines Manual, Version K, Jul. 12, 2002, pp. 1-34. [Accessed at http://www.med.unc.edu/pharm/sondeklab/Lab%20Resources/manuals/insect_cell_manual.pdf on Nov. 25, 2013].
Iowa State University, "Lyphoid Depletion: PCV2-Associated Lymphoid Depletion"., 2013, pp. 1-2. [Accessed at: http://vetmed.iastate.edu/research/labs/pcv2/pcv2-associated-disease/lymphoid-depleti . . . on Dec. 14, 2013].
Jensen et al., "Distinction between Porcine Circovirus Type 2 Enteritis and Porcine Proliferative Enteropathy caused by Lawsonia intracellularis". Journal of Comparative Pathology, vol. 135, 2006, pp. 176-182.
Jiang et al., "Expression, Self-Assembly, and Antigenicity of the Norwalk Virus Capsid Protein". Journal of Virology, vol. 66, No. 11, Nov. 1992, pp. 6527-6532.
Jiang et al., "Synthesis of rotavirus-Like Particles in Insect Cells: Comparative and Quantitative Analysis". Biotechnology and Bioengineering, vol. 60, No. 3, 1998, pp. 369-374.
Ju et al., "Immunogenicity of a recombinant pseudorabies virus expressing ORF1-ORF2 fusion protein of porcine circovirus type 2". 2005, Veterinary Microbiology, vol. 109, pp. 179-190.
Kamstrup, et al., "Immunisation against PCV2 structural protein by DNA vaccination of mice". 2004, Vaccine, vol. 22, pp. 1358-1361.
Kapust et al., "*Escherichia coli* maltose-binding protein is uncommonly effective at promoting the solubility of polypeptides to which it is fused". Protein Science, vol. 8, 1999, pp. 1668-1674.
Kennedy et al., "Repdocution of Lesions of Postweaning Multisystemic Wasting Syndrome by Infection of Conventional Pigs with Porcine Circovirus Type 2 Alone or in a Combination with Porcine Parvovirus". Journal of Comparative Pathology, vol. 122, 2000, pp. 9-24.
Kim et al., "A comparison of the Lymphocyte Subpopulations of Pigs Experimentally Infected with Porcine Circovirus 2 and/or Parvovirus". 2003, The Veterinary Journal, vol. 165, pp. 325-329.
Kim et al., "Association of Porcine Circovirus 2 with Porcine Respiratory Disese Complex", The Vet. Jour., 2003, 166, pp. 251-256.
Kim et al., "Characterization of the Recombinant Proteins of Porcine Circovirus Type2 Field Isolate Expressed in the Baculovirus System". 2002, Journal of Veterinary Science, vol. 3, No. 1, pp. 19-23.
Kim et al., "Efficacy of different disinfectants in vitro against porcine circovirus type 2". The Veterinary Record, vol. 164, May 2009, pp. 599-600.
Kim et al., "Enteritis associated with procine circovirus 2 in pigs". 2004, The Canadian Journal of Veterinary Research, vol. 68, pp. 218-221.
Kiupel, M. "Postweaning Multisystemic Wasting Syndrome (PMWS) in pigs". Production diseases in Farm Animals, 12th International Conference, Section D, Wageningen Academic Publishers, The Netherlands, 2006, pp. 74-89.
Kixmoller et al., "Reduction of PMWS-associated clinical signs and co-infections by vaccination against PCV2". 2008, Vaccine, vol. 26, pp. 3443-3451.
Kost, et al., "Recombinant baculoviruses as mammalian cell gene-delivery vectors". Apr. 2002, Trends in Biotechnology, vol. 20, No. 4, pp. 173-180.
Kovacs et al., "The live attenuated bovine viral diarrhea virus components of a multi-valent vaccine confer protection against fetal infection". Veterinary Microbiology, vol. 96, 2003, pp. 117-131.
Krakowka et al., "Features of porcine circovirus-2 disease: correlations between lesions, amount and distribution of virus, and clinical outcome". Journal of Veterinary Diagnostic Investigation, vol. 17, No. 3, May 2005, pp. 213-222.
Kyriakis et al., "The Effects of Immuno-modulation of the Clinical and Pathological Expression of Postweaning Multisystemic Wasting Syndrome". 2002, Journal of Comparative Pathology, vol. 126, pp. 38-46.
Kyriazakis et al., "The Maintenance of Health". Whittemore's Science and Practice of Pig Production, Third Edition, Chapter 7, Blackwell Publishing Ltd., Oxford, UK, 2006, pp. 263-316.
Riggs et al., "Efficacy of Monoclonal Antibodies against Defined Antigens for Passive Immunotherapy of Chronic Gastrointestinal Cryptosporidiosis". Antimicrobial Agents and Chemotherapy, vol. 46, No. 2, Feb. 2002, pp. 275-282.
Riggs et al., "Protective Monoclonal Antibody Defines a Circumsporozoite-Like Glycoprotein Exoantigen of Cryptosporidium parvum Sporozoites and Merozoites". The Journal of Immunology, vol. 158, 1997, pp. 1787-1795.
Rodríguez-Arrioja et al., "Dynamics of procine circovirus type 2 infection in a herd of pigs with postweaning multisystemic wasting syndrome". American Journal of Veterinary Research, vol. 63, No. 3, Mar. 2002, pp. 354-357.
Roesler et al., "Oral vaccination of pigs with an invasive gyrA-cpxA-rpoB *Salmonella typhimurium* mutant". Vaccine, vol. 23, No. 5, Dec. 2004, pp. 595-603.
Rotto, Hans "Diagnosis, Vaccination and Field Experiences with PCV-AD". Iowa Pork Progress, 2007, pp. 1-10.
Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.
Royer et al., "Susceptibility of porcine circovirus type 2 to commercial and laboratory disinfectants". Journal of Swine Health and Production, vol. 9, No. 6, 2001, pp. 281-284.
Rueda et al., "Effect of Different Baculovirus Inactivation Procedures on the Integrity and Immunogenicity of Porcine Parvovirus-Like Particles", Vaccine, 2001, 19, pp. 726-734.
Schaefer et al., "Characterization and Formulation of Multiple Epitope-Specific Neutralizing Monoclonal Antibodies for Passive Immunization against Cryptosporidiosis". Infection and Immunity, vol. 68, No. 5, May 2000, pp. 2608-2616.
Sedlik et al., "Recombinanat parvovirus-like particles as an antigen carrier: A novel nonreplicative exogenous antigen to elicit protective antiviral cytotoxic T cells". Proceedings of the National Academy of Sciences, vol. 94, Jul. 1997, pp. 7503-7508.
Segales et al., "Changes in Peripheral Blood Leukocyte Populations in Pigs with Natural Postweaning Multisystemic Wasting Syndrome (PMWS)", Vet. Immunology & Immunopathology, 2001, 81, pp. 37-44.

(56) References Cited

OTHER PUBLICATIONS

Segales et al., "Epidemiology of Porcine Circovirus Type 2 Infection: What do we Know?", Pig News & Information, 2003, vol. 24, No. 4, pp. 103N-110N.
Segales et al., "Granulomatous Enteritis and Lymphadenitis in Iberian Pigs Naturally Infected with Lawsonia intracellularis". Veterinary Pathology, vol. 38, No. 3, 2001, pp. 343-346.
Segales et al., "Pathological findings associated with naturally acquired porcine circovirus type 2 associated disease". Veterinary Microbiology, vol. 98, 2004, pp. 137-149.
Segales et al., "Postweaning Multisystemic Wasting Syndrome (PMWS) in Pigs, A Review", Vet. Quarterly, 2002, 24 (3), pp. 109-124.
Segalés et al., "Immunosuppression in postweaning multisystemic wasting syndrome affected pigs". Veterinary Microbiology, vol. 98, 2004, pp. 151-158.
Segalés et al., "Porcine Circovirus Diseases". Diseases of Swine, 9th Edition, Chapter 14, Blackwell Publishing, Ames, Iowa, 2006, pp. 299-307.
Segalés et al., "Postweaning Multisystemic Wasting Syndrome and Porcine Circovirus Ty;e 2: The European Perspective". Trends in Emerging Viral Infections of Swine, Ch. 9.3, PMWS and PCV2: European Perspective, 2002, pp. 297-303.
SEQ ID No. 11, Sequence Alignment with UniProt Database Accession No. O91862_PCV2 submitted Nov. 1998 by Meehan et al. (Journal of General Virology, 1998; 79: 2171-2179).
SEQ ID No. 11 Sequence Alignment with Geneseq Database Accession No. AAO23063 submitted Oct. 2003 in WO 2003049703, 2 pages.
SEQ ID No. 5 Sequence Alignment with Geneseq Database Accession No. ABB99415, submitted Jan. 2003 in WO2002/77210, 2 pages.
SEQ ID No. 5 Sequence Alignment with UniProt Database Accession No. Q9YTB6_PCV2 Submitted May 1999 by Fenaux et al. in Journal of Clinical Microbiology, 2000; 38: 2494-2503, 2 pages.
SEQ ID No. 6 Sequence Alignment with Geneseq Database Accession No. ADA9081 submitted Nov. 2003 in USPgPUB 2003/096377, 2 pages.
SEQ ID No. 6 Sequence Alignment with UniProt Database Accession No. Q9YTB6_PCV2 Submitted May 1999 by Fenaux et al. in Journal of Clinical Microbiology, 2000; 38: 2494-2503, 2 pages.
SEQ ID No. 3 Sequence Alignment with Geneseq Database Accession No. ABV72527 submitted Jan. 2003, in WO2002/077210, 3 pages.
SEQ ID No. 4 Sequence Alignment with Geneseq Database Accession No. ABV72527 submitted Jan. 2003, in WO2002/077210, 3 pages.
Shen et al., "Comparison of commercial and experimental porcine circovirus type 2 (PCV2) vaccines using a triple challenge with PCV2, porcine reproductive and respiratory syndrome virus (PRRSV), and porcine parvovirus (PPV)". Vaccine, vol. 28, 2010, pp. 5960-5966.
Sibila et al., "Use of a Polymerase Chain Reaction Assay and ELISA to Monitor Porcine Circovirus Type 2 Infection in Pigs From Farms with and without Postweaning Multisystemic Wasting jSyndrome", AJVR, Jan. 2004, vol. 65, No. 1, pp. 88-92.
Siebel, K. "PCV2 vaccination changing the pig industry Part 2. Global experiences from the field around one-shot vaccination". Pig Progress, vol. 26, No. 1, 2010, pp. 11-13.
Smith et al., "Observations on Experimental Oral Infection with *Salmonella dublin* in Calves and *Salmonella choleraesuis* in Pigs". Journal of Pathology and Bacteriology, vol. 93, No. 1, 1967, pp. 141-156.
Sorden et al., "Development of a Polyclonal-antibody-based Immunohystochemical Method for the Detection of Type 2 Porcine circovirus in Formalin-Fixed, Paraffin-Embedded Tissue", J. Vet Diagn. Inest, 1999, 11, pp. 528-530.
Spier, R.E., "Multivalent Vaccines: Prospects and Challenges". Folia Microbiologica, vol. 42, No. 2, 1997, pp. 105-112.
Suradhat et al., "The influence of maternal immunity on the efficacy of a classical swine fever vaccine against classical swine fever virus, genogroup 2.2, infection". Veterinary Microbiology, vol. 92, 2003, pp. 187-194.
Takada-Iwao et al., "Porcine circovirus type 2 (PCV2) vaccination reduces PCV2 in a PCV2 and *Salmonella enterica* serovar Choleraesuis coinfection model". Veterinary Microbiology, vol. 162, 2013, pp. 219-223.
Thacker et al., "Effect of vaccination on the potentiation of porcine reproductive and respiratory syndrom virus (PRRSV)-induced pneumonia by Mycoplama hyopneumoniae". Vaccine, vol. 18, 2000, pp. 1244-1252.
Thacker, Eileen L., "Diagnosis of Mycoplama hyopneumoniae". Journal of Swine Health Production, vol. 12, No. 5, 2004, pp. 252-254.
Thacker, Eileen L., "Mycoplasmal Diseases". Diseases of Swine, 9th Edition, Ch. 42, 2006, pp. 701-717.
Truong et al., "Identification of an immunorelevant ORF2 epitope from porcine circovirus type 2 as a serological marker for experimental and natural infection". Archives of Virology, vol. 146, 2001, pp. 1197-1211.
UniProt Database Accession No. O91862 submitted Nov. 1, 1998 by Meehan et al., Characterization of novel circovirus DNAs associated iwth wasting sydromes in pigs. Journal of General Virology, 1998; 79: 2171-2179, 1 page.
UniProt Database Accession No. Q9YTB6, Direct Submission, Wang et al., May 1, 1999 , 1 page.
Vansickle, J., "Circovirus Grips Industry". Jul. 15, 2006, National Hog Farmer.
Vasconcelos et al., "Swine and Poultry Pathogens: the Complete Genome Sequences of Two Strains of Mycoplasma hyopneumoniae and a Strain of Mycoplasma synoviae". Aug. 2005, Journal of Bacteriology, vol. 187, No. 16, pp. 5568-5577.
VIDO Swine Technical Group-Linking Knowledge to practical solutions "Vaccination Guidelines for Swine". Jun. 2004, www.vido.org.
Vincent et al., "Dendritic Cells Harbor Infetious Porcine Circovirus Type 2 in the Abscence of Apparent Cell Modulation or Replication of the Virus". Dec. 2003, Journal of Virology, vol. 77, No. 24, pp. 13288-13300.
Walker, et al., "Development and application of a competitive enzyme-linked immunosorbent assay for the detection of serum antibodies to porcine circovirus type 2". 2000, Journal of Veterinary Diagnostic Investigation, vol. 12, pp. 400-405.
Wan et al., "Comprehensive Prevention and Control Techniques for Porcine Circovirus Type 2 Infection". Chinese Swine Industry, No. 3, 2006, pp. 42-45.
Wang et al., "Construction and immunogenicity of recombinant adenovirus expressing the capsid protein of porcine circovirus 2 (PCV2) in mice". Vaccine, vol. 24, 2006, pp. 3374-3380.
WEB site: "Does stress-free livestock mean safer food?" http://www.foodnavigator.com/Financial-Industry/Does-stress-free-livestock-mean-safer-food Accessed on: Jun. 4, 2004.
Weibel, Helen, "A field efficacy study with Enterisol® Ileitis and Ingelvac CircoFLEX® in Switzerland". Universität Zürich, 2009, 1 page. [Accessed at: http://www.vet.uzh.ch/dissertationen/diss_anzeige.php?ID=724&sprache=e on Jun. 7, 2013].
Williams et al., "Combined vaccines and simultaneous administration: Current issues and perspectives". Annals of the New York Academy of Sciences, vol. 754, 1995, pp. xi-xv, 35-47.
Opriessnig et al., "Effect of porcine parvovirus vaccination on the development of PMWS in segregated early weaned pigs coinfected with type 2 porcine circovirus and porcine parvovirus". Veterinary Microbiology, vol. 98, 2004, pp. 209-220.
Belikov, V.G., "Connection between the molecular structure of substances and their action on organisms". Pharmaceutical Chemistry, vol. 1, Section 2.2, 1993, p. 43.
Mashkovski, M.D., "Interaction of Drugs". Medicaments, A Doctor's Manual, 14th Edition, vol. 1, Section 9, Moscow, 2001, p. 11.
Gupta et al., "Adjuvants for human vaccines-current status, problems and future prospects". Vaccine, vol. 13, No. 14, 1995, pp. 1263-1276.

(56) References Cited

OTHER PUBLICATIONS

Oh et al., "Evaluation of Two Different Vaccine Program Against M. Hyopneumniae on an 1100 Sow Farm in Korea". Asian Pig Veterinary Society Congress, Sep. 2013, 1 page.
Eichmeyer et al., "Efficacy evaluation of a Mycoplasma hyopneumoniae bacterin in a mixture with a porcine circovirus type 2 vaccine". Allen D. Leman Swine Conference-Recent Research Reports, 2008, pp. 28.
"Calendar, Mar. 2007". 3rd Annual Pig Veterinary Society Congress, vol. 37, No. 2, 2007, p. 33. [Accessed at http://www.piginternational-digital.com/piginternational/2007013//Print . . . on Aug. 3, 2012].
"General Methods 6xHis and GST Purification Direct Cloning". Baculovirus Expression Vector System Manual, 6th Edition, May 1999, pp. 1-108.
"H-V11-Postweaning multisystemic wasting syndrome-Lymph node—Pig". Read-Only Case Details Reviews: Mar. 2009, pp. 1-4. [Accessed at http://www.askjpc.org/vspo/show_page.php?id=800 on Dec. 14, 2013].
9 C.F.R. § 113.35 (2010).
Abstract in English of CN1458167, dated Nov. 26, 2003.
Albina et al., "An Experimental Model for Post-weaning Multisystenic Wasting Syndrome (PMWS) in Growing Piglets". 2001, Journal of Comparative Pathology, vol. 123, pp. 292-303.
Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.
Allan et al., "Letters, Immunostiulations, PCV-2 and PMWS", The Vet. Records, Aug. 5, 2000, pp. 170-171.
Allan et al., "Passive Transfer of Maternal Antibodies to PCV2 Protects Against Development of Post-weaning Multisystemic Wasting Syndrome (PMWS): Experiemental Infections and a Field Study". 2002, The Pig Journal, vol. 50, pp. 59-67.
Allan et al., "PCV2; ticking time bomb?" Pig Progress, vol. 18, No. 5, 2002, pp. 14-12.
Allan et al., "PMWS/PCVD: Diagnosis, Disease, and Control: What do we know?" 2006, Proceedings of the 19th IPVS Congress, Copenhagen, Denmark, vol. 1, pp. 1-9.
Allan et al., "Porcine Circoviruses; A Review", J. Vet., Diagn. Invest. 2000, 12, pp. 3-14.
Allan et al., "Reproduction of postweaning multisystemic wasting syndrome in pigs experimentally inoculated with a Swedish porcine circovirus 2 isolate". 2003, Journal of Veterinary Diagnostic Investigation, vol. 15, pp. 553-560.
Allan et al., Guest Editorial, "PCV-2 Infection in Swine; More Than Just Postweaning Multisystemic Wasting Syndrome", The Vet Journ., 2003, 166, pp. 222-223.
Bahnemann, Hans G., "Inactivation of Viruses in Serum with Binary Ethyleneimine". Journal of Clinical Microbiology, vol. 3, No. 2, Feb. 1976, pp. 209-210.
Banholzer, E. "A Follow-Up: PCV2, PRRS, Mycoplasma hyopneumoniae, Improvac". IPVS Congress, Jul. 16-19, 2006, pp. 1-20.
Bassaganya-Riera et al., "Conjugated Linoleic Acid Ameliorates Viral Infectivity in a Pig Model of Virally Induced Immunosuppression". 2003, American Society for Nutritional Sciences, pp. 3204-3214.
Beach et al., "Efficacy and future prospects of commercially available and experimental vaccines against porcine circovirus type 2 (PCV2)". Virus Research, vol. 164, 2012, pp. 33-42.
Begue et al., "Future Combined Vaccines". Journal of Infectious Diseases, vol. 173, Supp 3, 1996, pp. S295-S297.
Beseme et al., "Vaccination strategies for the control of circoviral diseases in pigs: PMWS and PCV2-associated PRDC". Proceedings of the Japanese Pig Veterinary Society, vol. 49, 2006, pp. 15-38.
Blanchard et al., "An ORF2 protein-based ELISA for porcine circovirus type 2 antibodies in post-weaning multisystemic wasting syndrome". Veterinary Microbiology, vol. 94, 2003, pp. 183-194.
Blanchard et al., "Protection of swine against post-weaning multisystemic wasting syndrome (PMWS) by porcine circovirus type 2 (PCV2) proteins". Vaccine, vol. 21, 2003, pp. 4565-4575.
Boehringer Ingelheim Vetmedica, Inc., "Data from studies consistent with maintaining safety and efficacy of Ingelvac CircoFLEXâ and Ingelvac MycoFLEXâ vaccines when mixed together and administered concurrently to pigs". Feb. 2008, Technical Bulletion, www.bi-vetmedica.com/swine-research/MycoFLEX-Mycoplasma-immunity_TB2.pdf; 14 pages.
Boehringer Ingelheim Vetmedica, Inc., Ingelvacâ Circoflexä Material Safety Data Sheet, Online Oct. 2006, pp. 1-10, URL:http://bi-vetmedica.com/sites/default/files/ingelvac-circoflex-msds.pdf.
Boisseson et al., "Molecular characterization of Porcine circovirus type 2 isolates from post-weaning multisystemic wasting syndrome-affected and non-affected pigs". 2004, Journal of General Virology, vol. 85, pp. 293-304.
Bolin et al., "Postweaning multisystemic wasting syndrome induced after experimental inoculation of cesarean-derived, colostrum-deprived piglets with type 2 porcine circovirus". 2001, Journal of Veterinary Diagnostice Investigation, vol. 13, pp. 185-194.
Bowie, et al., "Deciphering the Message in Protein Sequences: Tolerance to Amino Acid Substitutions," Science, vol. 247, 1990, pp. 1306-1310.
Brogden, Kim A., "Polymicrobial Diseases of Animals and Humans". Polymicrobial Diseases, Chapter 1, 2002, 19 pages. [Accessed at http://www.ncbi.nlm.nih.gov/books/NBK2477/?report=printable on Jul. 8, 2014].
Caprioli et al., "PCR detection of porcine circovirus type 2 (PCV2) DNA in blood, tonsillar and faecal swabs from experimentally infected pigs". Research in Veterinary Sciences, vol. 81, No. 2, Oct. 2006, pp. 287-292.
Chae, C. "A review of porcine circovirus 2-associated syndromes and diseases". The Veterinary Journal, vol. 169, No. 3, 2005, pp. 326-336.
Chae, C., "Postweaning multisystemic wasting syndrome: a review of aetiology, diagnosis and pathology". 2004, The Veterinary Journal, vol. 168, pp. 41-49.
Charbonneau, G., "Canadian Experiences with Porcine Circovirus Associated Disease". 2007, Iowa Pork Congress; 30 pages.
Chen et al., "Serological survey of serum antibodies against porcine circovirus type 2 (PCV2) in swine, chicken, duck, goat and cattle fromZhejiang province, China". Revue de Médecine Vétérinaire, vol. 158, Nos. 8-9, 2007, pp. 458-462.
Cheung et al., "Kinetics of Porcine Circovirus Type 2 Replication". Archives of Virology, vol. 147, 2002, pp. 43-58.
Chevez et al., "Long-term analysis of PCV2 prevalence in a Mexican herd using Ingelvac CircoFLES®". 22nd International Pig Veterinary Society Congress, Virology and Viral Diseases-PCV2, 2012, p. 908.
Chiou, et al., "The Effect of Porcine Circovirus Infection on the Immune Response of Pigs After Vaccination Against Classical Swine Fever and Pseudorabies". 2006, Proceedings of the 19th IPVS Congress, Copenhagen, Denmark, p. 79.
Chung et al., "Real-time PCR for quantitation of porcine reproductive and respiratory syndrome virus and porcine circovirus type 2 in naturally-infected and challenged pigs". Journal of Virological Methods , vol. 124, 2005, pp. 11-19.
Czermak et al., "Membrane Filtration in Animal Cell Cutlure". 2007, Methods in Biotechnology, vol. 24, pp. 397-420, Humana Press, New Jersey, USA.
Darwich et al., "Cytokine profiles of peripheral blood mononuclear cells from pigs with postweaning multisystemic wasting syndrome in response to mitogen, superantigen or recall viral antigens". 2003, Journal of General Virology, vol. 84, pp. 3453-3457.
Dawson et al., "Studies of the field efficacy and safety of a single-dose Mycoplasma hyopneumoniae vaccine for pigs". Veterinary Record, vol. 151, 2002, pp. 535-538.
Duarte et al., "Concomitant Zearalenone Ingestion and Porcine Circovirus-2 Infection". Acta Scientiae Veterinariae, vol. 41, Suppl. 1, Publication 37, 2013, pp. 1-6.

(56) References Cited

OTHER PUBLICATIONS

Dugdale et al., "Immune Response". Medline Plus Medicial Encyclopedia, Updated May 30, 2012, pp. 1-4. [Accessed at http://www.nlm.nih.gov/medlineplus/cncy/article/000821.htm on Mar. 19, 2014].
Ellis et al., "Lack of antibodies to porcine circovirus type 2 virus in beef and dairy cattle and horses in western Canada". Canadian Veterinary Journal, vol. 42, 2001, pp. 461-464.
Ellis et al., "Porcine circovirus-2 and concurrent infections in the field". Veterinary Microbiology, vol. 98, No. 2, Feb. 2004, pp. 159-163.
Ellis, John A., "Porcine circovirus: An old virus in a new guise causes an emerging disease thorugh a novel pathogenesis". Large Animal Veterinary Rounds, vol. 3, No. 4, Apr. 2003, pp. 1-6.
EMBL Acession No. ACA49861, Wang et al., "Porcine circovirus-2 capside protein". , Mar. 5, 2008, 1 page.
EMBL Acession No. ACA49867, Wang et al., "Porcine circovirus-2 capside protein". , Mar. 5, 2008, 1 page.
EMBL Acession No. ACV53224, Cortey et al., "Porcine circovirus-2 partial capsid protein". , Sep. 13, 2009, 1 page.
Fablet et al., "A Case Study of Neonatal Diarrhoea in a Farrow-to-Finish Pig Farm". International Society for Animal Hygiene, Saint Malo, 2004, p. 151.
Fachinger et al., "The effect of vaccination against porcine circovirus type 2 in pigs suffering from porcine respiratory disease complex". 2008, Vaccine, vol. 26, pp. 1488-1499.
Guedes et al., "Onset and duration of fecal shedding, cell-mediated and humoral immune responses in pigs after challenge with a pathogenic isolate or attenuated vaccine strain of Lawsonia intracellularis". Veterinary Microbiology, vol. 91, 2003, pp. 135-145.
Genbank Accession# AAC35299, ORF2 [Porcine circovirus], Sep. 13, 1998.
Pyle et al., "Secretion of biologically active human proapolipoprotein A-I in a baculovirus-insect cell system: protection from degradation by protease inhibitors". Journal of Lipid Research, vol. 36, 1995, pp. 2355-2361.
Boisgerault et al., "Virus-like particles: a new family of delivery systems". Expert Review of Vaccines, vol. 1, No. 1, Jun. 2002, pp. 101-109.
Weingartl et al., "Porcine circovirus structure and replication: a minireview". Agriculture, vol. 1, 2002, pp. 11-14.
Boga et al., "A single dose immunization with rabbit haemorrhagic disease virus major capsid protein produced in *Saccharomyces cerevisiae* induces protection". Journal of General Virology, vol. 78, 1997, pp. 2315-2318.
Bachmann et al., "The influence of virus structure on antibody responses and virus serotype formation". Immunology Today, vol. 17, No. 12, Dec. 1996, pp. 553-558.
Fan et al., "Baculovirus-Insect Expression and Immunological Studies of Porcin Circovirus Type 2 (PCV2) Capsid Protein". Proceedings of the 2nd Asian Pig Veterinary Society Congress, Sep. 19-21, 2005, Philippines, pp. 186-188.
Liljeqvist et al., "Production of recombinant subunit vaccines: protein immunogens, live delivery systems and nucleic acid vaccines". Journal of Biotechnology, vol. 73, 1999, pp. 1-33.
Invitrogen Life Technologies, "Guide to Baculovirus Express Vector Systems (BEVS) and Insect Cell Culture Techniques". Feb. 27, 2002, pp. 1-130. [Accessed at https://tools.thermofisher.com/content/sfs/manuals/bevtest.pdf].
Thacker et al. "Porcine Respiratory Disease Complex (PRDC)". Thai Journal of Veterinary Medicine, vol. 32, Supp., 2002, pp. 126-134.
Stoltenow, Charles L. "Getting the Most Out of a Vaccine Program". Proceedings, The Range Beef Cow Symposium XIX, Rapid City, SD, 2005, pp. 139-144.
Boehringer Ingelheim Vetmedica, Inc. "ImpranFLEX® Adjuvant: The advanced aqueous-based polymer adjuvant technology." [Accessed at : http://www.bi-vetmedica.com/species/swine/products/flex_vaccines/impranflex_adjuvant.html Retrieved on Sep. 28, 2016], pp. 1-2.

SEQUENCE LISTING

```
<160> NUMBER OF SEQ ID NOS: 11

<210> SEQ ID NO 1
<211> LENGTH: 8
<212> TYPE: DNA
<213> ORGANISM: Artificial
<220> FEATURE:
<223> OTHER INFORMATION: This is a modified Kozak's sequence

<400> SEQUENCE: 1

ccgccatg                                                                8


<210> SEQ ID NO 2
<211> LENGTH: 6
<212> TYPE: DNA
<213> ORGANISM: Artificial
<220> FEATURE:
<223> OTHER INFORMATION: This is a recombinant Eco R1 sequence.

<400> SEQUENCE: 2

gaattc                                                                  6


<210> SEQ ID NO 3
<211> LENGTH: 713
<212> TYPE: DNA
<213> ORGANISM: Porcine circovirus

<400> SEQUENCE: 3

cagctatgac gtatccaagg aggcgttacc gcagaagaag acaccgcccc cgcagccatc      60

ttggccagat cctccgccgc cgcccctggc tcgtccaccc ccgccaccgc taccgttgga     120

gaaggaaaaa tggcatcttc aacacccgcc tctcccgcac cttcggatat actgtggaga     180

aggaaaaatg gcatcttcaa cacccgcctc tcccgcacct tcggatatac tgtgacgact     240
```

-continued

```
ttgttccccc gggagggggg accaacaaaa tctctatacc ctttgaatac tacagaataa    300

gaaaggttaa ggttgaattc tggccctgct cccccatcac ccagggtgat aggggagtgg    360

gctccactgc tgttattcta gatgataact ttgtaacaaa ggccacagcc ctaacctatg    420

acccatatgt aaactactcc tcccgccata caatccccca acccttctcc taccactccc    480

gttacttcac acccaaacct gttcttgact ccactattga ttacttccaa ccaaataaca    540

aaaggaatca gctttggctg aggctacaaa cctctagaaa tgtggaccac gtaggcctcg    600

gcactgcgtt cgaaaacagt aaatacgacc aggactacaa tatccgtgta accatgtatg    660

tacaattcag agaatttaat cttaaagacc ccccacttaa accctaaatg aat           713


<210> SEQ ID NO 4
<211> LENGTH: 713
<212> TYPE: DNA
<213> ORGANISM: Porcine circovirus

<400> SEQUENCE: 4

ccgccatgac gtatccaagg aggcgttacc gcagaagaag acaccgcccc cgcagccatc     60

ttggccagat cctccgccgc cgcccctggc tcgtccaccc ccgccaccgc taccgttgga    120

gaaggaaaaa tggcatcttc aacacccgcc tctcccgcac cttcggatat actgtcaagg    180

ctaccacagt cacaacgccc tcctgggcgg tggacatgat gagatttaat attgacgact    240

ttgttccccc gggagggggg accaacaaaa tctctatacc ctttgaatac tacagaataa    300

gaaaggttaa ggttgaattc tggccctgct cccccatcac ccagggtgat aggggagtgg    360

gctccactgc tgttattcta gatgataact ttgtaacaaa ggccacagcc ctaacctatg    420

acccatatgt aaactactcc tcccgccata caatccccca acccttctcc taccactccc    480

gttacttcac acccaaacct gttcttgact ccactattga ttacttccaa ccaaataaca    540

aaaggaatca gctttggctg aggctacaaa cctctagaaa tgtggaccac gtaggcctcg    600

gcactgcgtt cgaaaacagt aaatacgacc aggactacaa tatccgtgta accatgtatg    660

tacaattcag agaatttaat cttaaagacc ccccacttga accctaagaa ttc           713


<210> SEQ ID NO 5
<211> LENGTH: 233
<212> TYPE: PRT
<213> ORGANISM: Porcine circovirus

<400> SEQUENCE: 5

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125
```

```
Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230


<210> SEQ ID NO 6
<211> LENGTH: 233
<212> TYPE: PRT
<213> ORGANISM: Porcine circovirus

<400> SEQUENCE: 6

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230


<210> SEQ ID NO 7
<211> LENGTH: 756
<212> TYPE: DNA
```

<213> ORGANISM: Artificial
<220> FEATURE:
<223> OTHER INFORMATION: This sequence is from porcine circovirus type 2, open reading frame 2, together with a portion from the pGEM T-easy vector.

<400> SEQUENCE: 7

```
gcggccgcgg gaattcgatc cgccatgacg tatccaagga ggcgttaccg cagaagaaga     60
caccgccccc gcagccatct tggccagatc ctccgccgcc gcccctggct cgtccacccc    120
cgccaccgct accgttggag aaggaaaaat ggcatcttca acacccgcct ctcccgcacc    180
ttcggatata ctgtcaaggc taccacagtc acaacgccct cctgggcggt ggacatgatg    240
agatttaata ttgacgactt tgttcccccg ggagggggga ccaacaaaat ctctataccc    300
tttgaatact acagaataag aaaggttaag gttgaattct ggccctgctc ccccatcacc    360
cagggtgata ggggagtggg ctccactgct gttattctag atgataactt tgtaacaaag    420
gccacagccc taacctatga cccatatgta aactactcct cccgccatac aatcccccaa    480
cccttctcct accactcccg ttacttcaca cccaaacctg ttcttgactc cactattgat    540
tacttccaac caaataacaa aaggaatcag ctttggctga ggctacaaac ctctagaaat    600
gtggaccacg taggcctcgg cactgcgttc gaaaacagta aatacgacca ggactacaat    660
atccgtgtaa ccatgtatgt acaattcaga gaatttaatc ttaaagaccc ccccacttgaa    720
ccctaagaat tctatcacta gtgaattcgc ggccgc                              756
```

<210> SEQ ID NO 8
<211> LENGTH: 10387
<212> TYPE: DNA
<213> ORGANISM: Artificial
<220> FEATURE:
<223> OTHER INFORMATION: This is the porcine circovirus type 2, ORF2 construct, which includes baculovirus and pGEM T-easy coding sequences.

<400> SEQUENCE: 8

```
aagctttact cgtaaagcga gttgaaggat catatttagt tgcgtttatg agataagatt     60
gaaagcacgt gtaaaatgtt tcccgcgcgt tggcacaact atttacaatg cggccaagtt    120
ataaaagatt ctaatctgat atgttttaaa acacctttgc ggcccgagtt gtttgcgtac    180
gtgactagcg aagaagatgt gtggaccgca gaacagatag taaaacaaaa ccctagtatt    240
ggagcaataa tcgatttaac caacacgtct aaatattatg atggtgtgca ttttttgcgg    300
gcgggcctgt tatacaaaaa aattcaagta cctggccaga ctttgccgcc tgaaagcata    360
gttcaagaat ttattgacac ggtaaaagaa tttacagaaa agtgtcccgg catgttggtg    420
ggcgtgcact gcacacacgg tattaatcgc accggttaca tggtgtgcag atatttaatg    480
cacaccctgg gtattgcgcc gcaggaagcc atagatagat tcgaaaaagc cagaggtcac    540
aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg gatattctcc accacaatgt tggcaacgtt gatgttacgt ttatgctttt    780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
```

-continued

```
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca aacatcgcaa aagccaatag   1800
tacagttttg atttgcatat taacggcgat tttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gtttttacga agcgatgaca   2520
tgacccccgt agtgacaacg atcacgccca aaagaactgc cgactacaaa attaccgagt   2580
atgtcggtga cgttaaaact attaagccat ccaatcgacc gttagtcgaa tcaggaccgc   2640
tggtgcgaga agccgcgaag tatggcgaat gcatcgtata acgtgtggag tccgctcatt   2700
agagcgtcat gtttagacaa gaaagctaca tatttaattg atcccgatga ttttattgat   2760
aaattgaccc taactccata cacggtattc tacaatggcg gggttttggt caaaatttcc   2820
ggactgcgat tgtacatgct gttaacggct ccgcccacta ttaatgaaat taaaaattcc   2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaaatattg   3000
aacgatttga aagaaaacaa tgtaccgcgc ggcggtatgt acaggaagag gtttatacta   3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatctttta   3180
atcaaatccc aagatgtgta taaaccacca aactgccaaa aaatgaaaac tgtcgacaag   3240
ctctgtccgt ttgctggcaa ctgcaagggt ctcaatccta tttgtaatta ttgaataata   3300
aaacaattat aaatgctaaa tttgtttttt attaacgata caaaccaaac gcaacaagaa   3360
```

-continued

```
catttgtagt attatctata attgaaaacg cgtagttata atcgctgagg taatatttaa   3420
aatcattttc aaatgattca cagttaattt gcgacaatat aattttattt tcacataaac   3480
tagacgcctt gtcgtcttct tcttcgtatt ccttctcttt ttcattttc tcctcataaa   3540
aattaacata gttattatcg tatccatata tgtatctatc gtatagagta aattttttgt   3600
tgtcataaat atatatgtct tttttaatgg ggtgtatagt accgctgcgc atagtttttc   3660
tgtaatttac aacagtgcta ttttctggta gttcttcgga gtgtgttgct ttaattatta   3720
aatttatata atcaatgaat ttgggatcgt cggttttgta caatatgttg ccggcatagt   3780
acgcagcttc ttctagttca attacaccat tttttagcag caccggatta acataacttt   3840
ccaaaatgtt gtacgaaccg ttaaacaaaa acagttcacc tcccttttct atactattgt   3900
ctgcgagcag ttgtttgttg ttaaaaataa cagccattgt aatgagacgc acaaactaat   3960
atcacaaact ggaaatgtct atcaatatat agttgctgat atcatggaga taattaaaat   4020
gataaccatc tcgcaaataa ataagtattt tactgttttc gtaacagttt tgtaataaaa   4080
aaacctataa atattccgga ttattcatac cgtcccacca tcgggcgcgg atcagatctg   4140
cagcggccgc gggaattcga tccgccatga cgtatccaag gaggcgttac cgcagaagaa   4200
gacaccgccc ccgcagccat cttggccaga tcctccgccg ccgcccctgg ctcgtccacc   4260
cccgccaccg ctaccgttgg agaaggaaaa atggcatctt caacacccgc ctctcccgca   4320
ccttcggata tactgtcaag gctaccacag tcacaacgcc ctcctgggcg gtggacatga   4380
tgagatttaa tattgacgac tttgttcccc cgggaggggg gaccaacaaa atctctatac   4440
cctttgaata ctacagaata agaaaggtta aggttgaatt ctggccctgc tcccccatca   4500
cccagggtga taggggagtg ggctccactg ctgttattct agatgataac tttgtaacaa   4560
aggccacagc cctaacctat gacccatatg taaactactc ctcccgccat acaatccccc   4620
aacccttctc ctaccactcc cgttacttca cacccaaacc tgttcttgac tccactattg   4680
attacttcca accaaataac aaaaggaatc agctttggct gaggctacaa acctctagaa   4740
atgtggacca cgtaggcctc ggcactgcgt tcgaaaacag taaatacgac caggactaca   4800
atatccgtgt aaccatgtat gtacaattca gagaatttaa tcttaaagac cccccacttg   4860
aaccctaaga attctatcac tagtgaattc gcggccgccg gccgctccag aattctagaa   4920
ggtacccggg atcctttcct gggacccggc aagaaccaaa aactcactct cttcaaggaa   4980
atccgtaatg ttaaacccga cacgatgaag cttgtcgttg gatggaaagg aaaagagttc   5040
tacagggaaa cttggacccg cttcatggaa gacagcttcc ccattgttaa cgaccaagaa   5100
gtgatggatg ttttccttgt tgtcaacatg cgtcccacta gacccaaccg ttgttacaaa   5160
ttcctggccc aacacgctct gcgttgcgac cccgactatg tacctcatga cgtgattagg   5220
atcgtcgagc cttcatgggt gggcagcaac aacgagtacc gcatcagcct ggctaagaag   5280
ggcggcggct gcccaataat gaaccttcac tctgagtaca ccaactcgtt cgaacagttc   5340
atcgatcgtg tcatctggga gaacttctac aagcccatcg tttacatcgg taccgactct   5400
gctgaagagg aggaaattct ccttgaagtt tccctggtgt tcaaagtaaa ggagtttgca   5460
ccagacgcac ctctgttcac tggtccggcg tattaaaaca cgatacattg ttattagtac   5520
atttattaag cgctagattc tgtgcgttgt tgatttacag acaattgttg tacgtatttt   5580
aataattcat taaatttata atctttaggg tggtatgtta gagcgaaaat caaatgattt   5640
tcagcgtctt tatatctgaa tttaaatatt aaatcctcaa tagatttgta aaataggttt   5700
cgattagttt caaacaaggg ttgtttttcc gaaccgatgg ctggactatc taatggattt   5760
```

```
tcgctcaacg ccacaaaact tgccaaatct tgtagcagca atctagcttt gtcgatattc   5820
gtttgtgttt tgttttgtaa taaaggttcg acgtcgttca aaatattatg cgcttttgta   5880
tttctttcat cactgtcgtt agtgtacaat tgactcgacg taaacacgtt aaataaagct   5940
tggacatatt taacatcggg cgtgttagct ttattaggcc gattatcgtc gtcgtcccaa   6000
ccctcgtcgt tagaagttgc ttccgaagac gattttgcca tagccacacg acgcctatta   6060
attgtgtcgg ctaacacgtc cgcgatcaaa tttgtagttg agctttttgg aattatttct   6120
gattgcgggc gtttttgggc gggtttcaat ctaactgtgc ccgattttaa ttcagacaac   6180
acgttagaaa gcgatggtgc aggcggtggt aacatttcag acggcaaatc tactaatggc   6240
ggcggtggtg gagctgatga taaatctacc atcggtggag gcgcaggcgg ggctggcggc   6300
ggaggcggag gcggaggtgg tggcggtgat gcagacggcg gtttaggctc aaatgtctct   6360
ttaggcaaca cagtcggcac ctcaactatt gtactggttt cgggcgccgt ttttggtttg   6420
accggtctga gacgagtgcg atttttttcg tttctaatag cttccaacaa ttgttgtctg   6480
tcgtctaaag gtgcagcggg ttgaggttcc gtcggcattg gtggagcggg cggcaattca   6540
gacatcgatg gtggtggtgg tggtggaggc gctggaatgt taggcacggg agaaggtggt   6600
ggcggcggtg ccgccggtat aatttgttct ggtttagttt gttcgcgcac gattgtgggc   6660
accggcgcag gcgccgctgg ctgcacaacg gaaggtcgtc tgcttcgagg cagcgcttgg   6720
ggtggtggca attcaatatt ataattggaa tacaaatcgt aaaaatctgc tataagcatt   6780
gtaatttcgc tatcgtttac cgtgccgata tttaacaacc gctcaatgta agcaattgta   6840
ttgtaaagag attgtctcaa gctcgccgca cgccgataac aagccttttc atttttacta   6900
cagcattgta gtggcgagac acttcgctgt cgtcgacgta catgtatgct ttgttgtcaa   6960
aaacgtcgtt ggcaagcttt aaaatattta aaagaacatc tctgttcagc accactgtgt   7020
tgtcgtaaat gttgtttttg ataatttgcg cttccgcagt atcgacacgt tcaaaaaatt   7080
gatgcgcatc aattttgttg ttcctattat tgaataaata agattgtaca gattcatatc   7140
tacgattcgt catggccacc acaaatgcta cgctgcaaac gctggtacaa ttttacgaaa   7200
actgcaaaaa cgtcaaaact cggtataaaa taatcaacgg gcgctttggc aaaatatcta   7260
ttttatcgca caagcccact agcaaattgt atttgcagaa aacaatttcg gcgcacaatt   7320
ttaacgctga cgaaataaaa gttcaccagt taatgagcga ccacccaaat tttataaaaa   7380
tctattttaa tcacggttcc atcaacaacc aagtgatcgt gatggactac attgactgtc   7440
ccgatttatt tgaaacacta caaattaaag gcgagctttc gtaccaactt gttagcaata   7500
ttattagaca gctgtgtgaa gcgctcaacg atttgcacaa gcacaatttc atacacaacg   7560
acataaaact cgaaaatgtc ttatatttcg aagcacttga tcgcgtgtat gtttgcgatt   7620
acggattgtg caaacacgaa aactcactta gcgtgcacga cggcacgttg gagtatttta   7680
gtccggaaaa aattcgacac acaactatgc acgtttcgtt tgactggtac gcggcgtgtt   7740
aacatacaag ttgctaacgt aatcatggtc atagctgttt cctgtgtgaa attgttatcc   7800
gctcacaatt ccacacaaca tacgagccgg aagcataaag tgtaaagcct ggggtgccta   7860
atgagtgagc taactcacat taattgcgtt gcgctcactg cccgctttcc agtcgggaaa   7920
cctgtcgtgc cagctgcatt aatgaatcgg ccaacgcgcg gggagaggcg gtttgcgtat   7980
tgggcgctct tccgcttcct cgctcactga ctcgctgcgc tcggtcgttc ggctgcggcg   8040
agcggtatca gctcactcaa aggcggtaat acggttatcc acagaatcag gggataacgc   8100
```

-continued

```
aggaaagaac atgtgagcaa aaggccagca aaaggccagg aaccgtaaaa aggccgcgtt   8160
gctggcgttt ttccataggc tccgcccccc tgacgagcat cacaaaaatc gacgctcaag   8220
tcagaggtgg cgaaacccga caggactata aagataccag gcgtttcccc ctggaagctc   8280
cctcgtgcgc tctcctgttc cgaccctgcc gcttaccgga tacctgtccg cctttctccc   8340
ttcgggaagc gtggcgcttt ctcatagctc acgctgtagg tatctcagtt cggtgtaggt   8400
cgttcgctcc aagctgggct gtgtgcacga accccccgtt cagcccgacc gctgcgcctt   8460
atccggtaac tatcgtcttg agtccaaccc ggtaagacac gacttatcgc cactggcagc   8520
agccactggt aacaggatta gcagagcgag gtatgtaggc ggtgctacag agttcttgaa   8580
gtggtggcct aactacggct acactagaag gacagtattt ggtatctgcg ctctgctgaa   8640
gccagttacc ttcggaaaaa gagttggtag ctcttgatcc ggcaaacaaa ccaccgctgg   8700
tagcggtggt ttttttgttt gcaagcagca gattacgcgc agaaaaaaag gatctcaaga   8760
agatcctttg atcttttcta cggggtctga cgctcagtgg aacgaaaact cacgttaagg   8820
gattttggtc atgagattat caaaaaggat cttcacctag atccttttaa attaaaaatg   8880
aagttttaaa tcaatctaaa gtatatatga gtaaacttgg tctgacagtt accaatgctt   8940
aatcagtgag gcacctatct cagcgatctg tctatttcgt tcatccatag ttgcctgact   9000
ccccgtcgtg tagataacta cgatacggga gggcttacca tctggcccca gtgctgcaat   9060
gataccgcga gacccacgct caccggctcc agatttatca gcaataaacc agccagccgg   9120
aagggccgag cgcagaagtg gtcctgcaac tttatccgcc tccatccagt ctattaattg   9180
ttgccgggaa gctagagtaa gtagttcgcc agttaatagt ttgcgcaacg ttgttgccat   9240
tgctacaggc atcgtggtgt cacgctcgtc gtttggtatg gcttcattca gctccggttc   9300
ccaacgatca aggcgagtta catgatcccc catgttgtgc aaaaaagcgg ttagctcctt   9360
cggtcctccg atcgttgtca gaagtaagtt ggccgcagtg ttatcactca tggttatggc   9420
agcactgcat aattctctta ctgtcatgcc atccgtaaga tgcttttctg tgactggtga   9480
gtactcaacc aagtcattct gagaatagtg tatgcggcga ccgagttgct cttgcccggc   9540
gtcaatacgg gataataccg cgccacatag cagaacttta aaagtgctca tcattggaaa   9600
acgttcttcg gggcgaaaac tctcaaggat cttaccgctg ttgagatcca gttcgatgta   9660
acccactcgt gcacccaact gatcttcagc atcttttact ttcaccagcg tttctgggtg   9720
agcaaaaaca ggaaggcaaa atgccgcaaa aaagggaata agggcgacac ggaaatgttg   9780
aatactcata ctcttccttt ttcaatatta ttgaagcatt tatcagggtt attgtctcat   9840
gagcggatac atatttgaat gtatttagaa aaataaacaa ataggggttc cgcgcacatt   9900
tccccgaaaa gtgccacctg acgtctaaga aaccattatt atcatgacat taacctataa   9960
aaataggcgt atcacgaggc cctttcgtct cgcgcgtttc ggtgatgacg gtgaaaacct  10020
ctgacacatg cagctcccgg agacggtcac agcttgtctg taagcggatg ccgggagcag  10080
acaagcccgt cagggcgcgt cagcgggtgt tggcgggtgt cggggctggc ttaactatgc  10140
ggcatcagag cagattgtac tgagagtgca ccatatgcgg tgtgaaatac cgcacagatg  10200
```

-continued

```
cgtaaggaga aaataccgca tcaggcgcca ttcgccattc aggctgcgca actgttggga  10260

agggcgatcg gtgcgggcct cttcgctatt acgccagctg gcgaaagggg gatgtgctgc  10320

aaggcgatta agttgggtaa cgccagggtt ttcccagtca cgacgttgta aaacgacggc  10380

cagtgcc                                                            10387


<210> SEQ ID NO 9
<211> LENGTH: 20
<212> TYPE: PRT
<213> ORGANISM: Porcine circovirus

<400> SEQUENCE: 9

Ser Tyr Pro Arg Arg Arg Tyr Arg Arg Arg Arg His His Pro Pro Ser
1               5                   10                  15

His Leu Gly Gln
            20


<210> SEQ ID NO 10
<211> LENGTH: 19
<212> TYPE: PRT
<213> ORGANISM: Porcine circovirus

<400> SEQUENCE: 10

Pro Arg His His Tyr Arg Pro Arg Arg Lys Asn Gly Ile Phe Asn Thr
1               5                   10                  15

Thr Leu Ser


<210> SEQ ID NO 11
<211> LENGTH: 233
<212> TYPE: PRT
<213> ORGANISM: Artificial
<220> FEATURE:
<223> OTHER INFORMATION: This is an amino acid sequence for porcine
      circovirus type 2, open reading frame 2.

<400> SEQUENCE: 11

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Lys Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175
```

-continued

```
Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

PCV2 *MYCOPLASMA HYOPNEUMONIAE* IMMUNOGENIC COMPOSITIONS AND METHODS OF PRODUCING SUCH COMPOSITIONS

RELATED APPLICATIONS

This application claims the priority benefit of U.S. provisional application Ser. No. 61/023,086, filed on Jan. 23, 2008 and U.S. provisional Ser. No. 61/025,293, filed on Jan. 31, 2008. The teachings and content of both of these applications are hereby incorporated by reference herein.

BACKGROUND OF THE INVENTION

Field of the Invention

In one aspect of the present invention, an immunogenic composition effective for inducing an immune response against infection by *Mycoplasma hyopneumoniae* (*M. hyo*) is provided. More particularly, the present invention is concerned with an immunogenic composition effective for inducing, eliciting, or providing an immune response that protects an animal receiving such a composition and reduces the incidence of, or lessens the severity of, the clinical symptoms associated with *M. hyo* infection. Still more particularly, the present invention is concerned with an immunogenic composition that includes therein cell-based antigen, preferably a bacterin, which confers a protective immune response against infection by *M. hyo*. Even more particularly, the present invention is concerned with an immunogenic composition comprising *M. hyo* bacterin, wherein administration of the bacterin results in a protective immune response against infection by *M. hyo*. Most particularly, the present invention is concerned with an immunogenic composition effective for conferring a protective immune response to a swine receiving the immunogenic composition, and wherein a dose of the composition comprises *M. hyo* bacterin with a relative potency (RP) of at least 1.22. Additionally, methods for producing and administering such immunogenic compositions are provided.

In another aspect of the present invention, an immunogenic composition effective for inducing an immune response against infection by porcine circovirus 2 (PCV2) is provided. More particularly, the present invention is concerned with an immunogenic composition effective for providing an immune response that protects an animal receiving the composition by reducing the incidence of, or lessening the severity of the clinical symptoms associated with PCV2 infection. Still more particularly, the present invention is concerned with a protein-based immunogenic composition that confers a protective immune response against infection by PCV2. Even more particularly, the present invention is concerned with an immunogenic composition comprising ORF2 of PCV2, wherein administration of PCV2-ORF2 results in a protective immune response against infection by PCV2. Most particularly, the present invention is concerned with an immunogenic composition effective for conferring a protective immune response to a swine receiving the immunogenic composition, and wherein the composition comprises the protein expressed by ORF2 of PCV2 and has an RP value of at least 1.38. Additionally, the present invention provides methods for producing and administering such immunogenic compositions.

In another aspect of the present invention, a combination immunogenic composition, combination vaccine, or multivalent immunogenic composition or vaccine is provided. More particularly, the present invention provides immunogenic compositions effective at inducing an immune response against infection by *M. hyo* and at least one other disease-causing organism for swine. Even more particularly, the present invention provides a composition effective at inducing an immune response against infection by *M. hyo* and inducing an immune response against infection by PCV2. Preferably, the immune response against *M. hyo* and PCV2 is sufficient to reduce the severity of or incidence of clinical signs or symptoms associated with each respective pathogen up to and including preventing the same. In preferred forms of such an immunogenic composition, the *M. hyo* portion thereof will have an RP value of at least 1.22 and the PCV2 portion thereof will also have an RP value of at least 1.38. The present invention further provides methods of producing and administering such compositions.

Description of the Prior Art

*Mycoplasma hyopneumoniae* is a small bacterium (400-1200 nm) classified in the mycoplasmataceae family. *M. hyo* is associated with Enzootic Pneumonia, a swine respiratory disease commonly seen in growing and finishing pigs. *M. hyo* attacks the cilia of epithelial cells of the windpipe and lungs, causing the cilia to stop beating (ciliostasis) and eventually causing areas of the lungs to collapse. Depending on the extent of the disease, daily live weight gain of infected swine can be reduced by up to 17%. Enzootic Pneumonia is widespread in swine populations and present in almost every swine herd. *M. hyo* is considered to be a primary pathogen that facilitates entry of PRRSV and other respiratory pathogens into the lungs. Three separate strains, 232, J, & 7448, have had their genomes sequenced (Minion et al., J. Bacteriol. 186: 7123-33, 2004; Vasconcelos et al., J. Bacteriol. 187: 5568-77, 2005). Clinical signs of *M. hyo* infection include a dry cough, impaired performance, and lung lesions.

Porcine circovirus type 2 (PCV2) is a small (17-22 nm in diameter), icosahedral, non-enveloped DNA virus, which contains a single-stranded circular genome. PCV2 shares approximately 80% sequence identity with porcine circovirus type 1 (PCV1). However, in contrast with PCV1, which is generally non-virulent, swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In some affected swine, a combination of all symptoms will be apparent while other swine will only have one or two of these symptoms. During necropsy, microscopic and macroscopic lesions also appear on multiple tissues and organs, with lymphoid organs being the most common site for lesions. A strong correlation has been observed between the amount of PCV2 nucleic acid or antigen and the severity of microscopic lymphoid lesions. Mortality rates for swine infected with PCV2 can approach 80%. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia.

Open reading frame 2 (ORF2) protein of PCV2, having an approximate molecular weight of 30 kDa when run on SDS-PAGE gel, has been utilized in the past as an antigenic component in vaccines for PCV2. Typical methods of obtaining ORF2 for use in such vaccines generally consist of amplifying the PCV2 DNA coding for ORF2, transfecting a viral vector with the ORF2 DNA, infecting cells with the viral vector containing the ORF2 DNA, permitting the virus to express ORF2 protein within the cell, and extracting the ORF2 protein from the cell via cell lysis. These procedures generally take up to about four days after infection of the cells by the viral vector. However, these procedures have a disadvantage in that the extraction procedures are both costly and time-consuming. Additionally, the amount of ORF2 recovered from the cells is not very high; consequently, a large number of cells need to be infected by a large number of viral vectors in order to obtain sufficient quantities of the recombinant expressed protein for use in vaccines and the like.

Accordingly, what is needed in the art is an immunogenic composition that confers a protective immune response against, reduces the incidence of, and/or lessens the severity of or prevents the clinical signs associated with PCV2 infection and *M. hyo* infection. In particular, what is needed in the art is a combination vaccine comprising *M. hyo* antigen and PCV-2 antigen in sufficient amounts to confer a protective immune response against, reduces the incidence of, and/or lessens the severity of or prevents the clinical signs associated with PCV2 infection and *M. hyo* infection after a single administration of such vaccine. Such a vaccine would improve the compliance of swine vaccines.

SUMMARY OF THE INVENTION

The present invention overcomes the problems inherent in the prior art and provides a distinct advance in the state of the art. In one aspect of the present invention, an immunogenic composition for eliciting a protective immune response in a pig against *M. hyo* is provided. Preferably, the immunogenic composition comprises porcine circovirus type 2 antigen and *M. hyo* antigen. Even more preferably, the amount of the *M. hyo* antigen in each dose has a relative potency (RP) value of at least 1.22, wherein a relative potency value of 1.22 means that at least 95% and preferably 100% of mice receiving an administration of one-fortieth (1/40) of such amount of *M. hyo* antigen develop a detectable amount of antibodies within or at 21 days post treatment in a *M. hyo* specific antibody detection assay. Thus, the 40-fold amount of *M. hyo* antigen that is needed to induce a detectable *M. hyo* specific antibody response in at least 95% and preferably 100% of mice within or at 21 days post treatment is sufficient to confer a protective immune response against, reduces the incidence of, and/or lessens the severity of or prevents the clinical signs associated with a *M. hyo* infection, when administered together with a porcine circovirus type 2 antigen. In other words the amount of *M. hyo* antigen as described above has been shown to be able to overcome any negative interference with the PCV2 antigen, when mixed and administered as a combination vaccine. Consequently, the present invention also relates to an immunogenic composition comprising porcine circovirus type 2 antigen and *M. hyo* antigen, wherein the amount of the *M. hyo* antigen per dose has a relative potency (RP) value of at least 1.22, wherein said RP value of 1.22 corresponds to the 40-fold amount of *M. hyo* antigen, that is needed to induce a detectable *M. hyo* specific antibody response in at least 95% and preferably 100% of mice within or at 21 days post treatment. In some preferred forms, the composition further includes or comprises an adjuvant. A variety of adjuvants will be useful with the present invention and can be selected by those of skill in the art, but carbomer and even more preferably CARBOPOL™ (high molecular weight cross-linked polyacrylic acid polymer) are particularly preferred. Advantageously, the immunogenic composition of the present invention confer a protective immune response against, reduces the incidence of, and/or lessens the severity of or prevents the clinical signs associated with a *M. hyo* infection when administered to a pig as a single dose administration. Such a single dose elicits a duration of immunity of at least 100, more preferably at least 110, even more preferably at least 120, still more preferably at least 130, even more preferably at least 140, still more preferably at least 150, even more preferably at least 160, still more preferably at least 170, even more preferably at least 180, and most preferably at least 184 days when administered to a pig. In other words, one dose of the immunogenic composition of the present invention, without boosters or subsequent doses, provides an animal or group of animals with a reduced incidence of or lessened severity of clinical signs of infection from *M. hyo* for at least 100 (110, 120, 130, 140, 150, 160, 170, 180, etc) and most preferably at least 184 days. With respect to the antibody detection assay, those of skill in the art will be able to identify and utilize appropriate products. ELISA assays and especially the IDEXX Herdchek *M. hyo* Test Kit™ (IDEXX Laboratories, Inc., Westbrook, Me.) are preferred. In particular, the IDEXX Herdchek *M. hyo* Test Kit™ (IDEXX Laboratories, Inc., Westbrook, Me.) was used as a reference assay according to the present invention.

In another aspect of the present invention, an immunogenic composition for eliciting a protective immune response in a pig against PCV2 is provided. Preferably, the immunogenic composition comprises porcine circovirus type 2 antigen and *M. hyo* antigen. Even more preferably, the amount of the PCV2 antigen in each dose has a relative potency (RP) value of at least 1.38, wherein a relative potency value of 1.38 means that at least 85% of mice receiving an administration of one-twentieth (1/20) of such amount of PCV2 antigen develop a detectable amount of antibodies within or at 21 days post treatment in a PCV2 specific antibody detection assay. Preferably, a relative potency value of 1.38 means that at least 95% and preferably 100% of mice receiving an administration of one-tenth (1/10) of such amount of PCV2 antigen develop a detectable amount of antibodies within or at 21 days post treatment in a PCV2 specific antibody detection assay. Thus the 20-fold amount of PCV2 antigen that is needed to induce a detectable PCV2 specific antibody response in at least 85% of the mice within or at 21 days post treatment or preferably the 10-fold amount of PCV2 antigen that is needed to induce a detectable PCV2 specific antibody response in at least 95% and preferably 100% of the mice within or at 21 days post treatment has been shown to be sufficient to confer a protective immune response against, reduce the incidence of, and/or lessen the severity of or prevent the clinical signs associated with a PCV2 infection, when administered together with a *M. hyo* antigen. In other words the amount of PCV2 antigen as described above has been shown to be able to overcome any negative interference with the *M. hyo* antigen, when mixed and administered as a combination vaccine. Consequently, the present invention also relates to an immunogenic composition comprising porcine circovirus type 2 antigen and *M. hyo* antigen, wherein the amount of the PCV2 antigen per dose has a relative potency (RP) value of at least 1.38, wherein said RP value of 1.38 corresponds to the 20-fold amount of PCV2 antigen that is needed to induce a detectable PCV2 specific antibody response in at least 85% of mice within or at 21 days post treatment. According to another aspect, the present invention also relates to an immunogenic composition comprises porcine circovirus type 2 antigen and *M. hyo* antigen, wherein the amount of the PCV2 antigen per dose has a relative potency (RP) value of at least 1.38, wherein said RP value of 1.38 corresponds to the 10-fold amount of PCV2 antigen, that is needed to induce a detectable PCV2 specific antibody response in at least 95% and preferably 100% of mice within or at 21 days post treatment.

In some preferred forms of this embodiment, the composition further includes or comprises an adjuvant. A variety of adjuvants will be useful with the present invention and can be selected by those of skill in the art, but carbomer and even more preferably CARBOPOL™ are particularly preferred. Advantageously, the immunogenic compositions of the present invention confer a protective immune response against, reduce the incidence of, and/or lessen the severity of or prevent the clinical signs associated with a PCV2 infection when administered to a pig as a single dose administration. Such a single dose elicits a duration of immunity of at least 100, more preferably at least 110, even more preferably at least 120, still more preferably at least 130, even more preferably at least 140, still more preferably at least 150, even more preferably at least 160, still more preferably at least 170, even more preferably at least 180, and most preferably at least 184 days when administered to a pig. In other words, one dose of the immunogenic composition of the present invention, without boosters or subsequent doses, provides an animal or group of animals with a reduced incidence of or lessened severity of clinical signs of infection from PCV2 for at least 100 (110, 120, 130, 140, 150, 160, 170, 180, etc) and most preferably for at least 184 days. With respect to the antibody detection assay, those of skill in the art will be able to identify and utilize appropriate methods and products. ELISA assays and the procedures described by Nawagitgul, P., et al. (the teachings and content of which are hereby incorporated by reference) in *Modified indirect porcine circovirus* (*PCV*) *type* 2-*based and recombinant capsid protein* (*ORF*2)-*based ELISA for the detection of antibodies to* PCV Clin. Diagn. Lab. Immunol. 9:33-40 (2002), are particularly preferred.

In other aspect of the present invention, an immunogenic composition comprising an effective amount of *M. hyo* antigen and an effective amount of PCV2 antigen is provided. Preferably, both the *M. hyo* antigen and the PCV2 antigen will have an RP value of at least 1.22 and 1.38, respectively, as described above wherein an RP value of 1.22 for *M. hyo* and 1.38 for PCV2 means that 95% and preferably 100% of mice receiving an administration of one-fortieth of such amount of *M. hyo* and one-tenth of such amount of PCV2 antigen develop a detectable amount of antibodies within or at 21 days post treatment in an *M. hyo* and PCV2 specific antibody detection assay. Thus the 40-fold amount of *M. hyo* antigen that is needed to induce a detectable *M. hyo* specific antibody response in at least 95% and preferably 100% of mice within or at 21 days post treatment and the 10-fold amount of PCV2 antigen that is needed to induce a detectable PCV2 specific antibody response in at least 95% and preferably 100% of mice within or at 21 days post treatment have been shown to be sufficient to confer a protective immune response against, reduce the incidence of, and/or lessen the severity of or prevent the clinical signs associated with a PCV2 infection and/or *M. hyo* infection, when administered together with a *M. hyo* antigen. In other words the amounts of PCV2 antigen and *M. hyo* antigen as described above have been shown to be able to overcome any negative interference between both antigens, when mixed and administered as a combination vaccine. Consequently, the present invention also relates to an immunogenic composition comprising porcine circovirus type 2 antigen and *M. hyo* antigen, wherein the amount of the *M. hyo* and PCV2 antigen per dose has a relative potency value of at least 1.22 and 1.38 respectively, wherein said RP value of 1.22 for the *M. hyo* antigen corresponds to the 40-fold amount of *M. hyo* antigen that is needed to induce a detectable *M. hyo* specific antibody response in at least 95% and preferably 100% of mice within or 21 days post treatment and wherein said RP value of 1.38 for the PCV2 antigen corresponds to the 20-fold amount of PCV2 antigen that is needed to induce a detectable PCV2 specific antibody response in at least 85% of mice within or 21 days post treatment. Preferably, said RP value of 1.38 for the PCV2 antigen corresponds to the 10-fold amount of PCV2 antigen that is needed to induce a detectable PCV2 specific antibody response in at least 95% and preferably 100% of mice within or at 21 days post treatment. In some preferred forms of this embodiment, the composition further includes or comprises an adjuvant. A variety of adjuvants will be useful with the present invention and can be selected by those of skill in the art, but carbomer and especially CARBOPOL™ are particularly preferred. Advantageously, the immunogenic composition of the present invention elicits a protective immune response when administered to a pig as a single dose administration. Such a single dose elicits a duration of immunity of at least 100, more preferably at least 110, even more preferably at least 120, still more preferably at least 130, even more preferably at least 140, still more preferably at least 150, even more preferably at least 160, still more preferably at least 170, even more preferably at least 180, and most preferably at least 184 days when administered to a pig. In other words, one dose of the immunogenic composition of the present invention, without boosters or subsequent doses, provides an animal or group of animals with a reduced incidence of or lessened severity of clinical signs of infection from *M. hyo* and PCV2 for at least 100 (110, 120, 130, 140, 150, 160, 170, 180, etc) and most preferably for at least 184 days. With respect to the antibody detection assay, those of skill in the art will be able to identify and utilize appropriate methods and products. ELISA assays and the procedures described by Nawagitgul, P., et al. (the teachings and content of which are hereby incorporated by reference) in *Modified indirect porcine circovirus* (*PCV*) *type* 2-*based and recombinant capsid protein* (*ORF*2)-*based ELISA for the detection of antibodies to* PCV Diagn. Lab. Immunol. 9:33-40 (2002), are particularly preferred for a PCV2 antibody detection assay and the IDEXX Herdchek *M hyo* Test Kit™ is particularly preferred for the *M. hyo* antibody detection assay.

In another aspect of the present invention, a method for eliciting a protective immune response in a pig against *M. hyo* is provided. Generally, the method comprises the step of administering an immunogenic composition in accordance with the present invention to an animal in need thereof, preferably a pig. Preferably, the immunogenic composition comprises porcine circovirus type 2 antigen and *M. hyo* antigen. Even more preferably, the amount of the *M. hyo* antigen in each dose has a relative potency (RP) value of at least 1.22, wherein an RP value of 1.22 for *M. hyo* means that 95% and preferably 100% of mice receiving an administration of one-fortieth of such amount of *M. hyo* antigen develop a detectable amount of antibodies within or at 21 days post treatment in an *M. hyo* specific antibody detection assay. Consequently, the present invention also relates to method for eliciting a protective immune response in a pig against *Mycoplasma hyopneumoniae* (*M. hyo*) comprising administering to said pig an immunogenic composition which comprises porcine circovirus type 2 antigen and *M. hyo* antigen, wherein the amount of the *M. hyo* antigen per dose has a relative potency value of at least 1.22, wherein said RP value of 1.22 corresponds to the 40-fold amount of *M. hyo* antigen that is needed to induce a detectable *M. hyo* specific antibody response in at least 95% and preferably 100% of mice within or at 21 days post treatment. In some preferred forms, the composition further includes or comprises an adjuvant. A variety of adjuvants will be useful with the present invention and can be selected by those of skill in the art, but carbomer, and even more preferably CARBOPOL™, are particularly preferred. Advantageously, the immunogenic composition of the present invention elicits a protective immune response when administered to a pig as a single dose administration. Such a single dose elicits a duration of immunity of at least 100, more preferably at least 110, even more preferably at least 120, still more preferably at least 130, even more preferably at least 140, still more preferably at least 150, even more preferably at least 160, still more preferably at least 170, even more preferably at least 180, and most preferably at least 184 days when administered to a pig. In other words, one dose of the immunogenic composition of the present invention, without boosters or subsequent doses, provides an animal or group of animals with a reduced incidence of or lessened severity of clinical signs of infection from *M. hyo* for at least 100 (110, 120, 130, 140, 150, 160, 170, 180, etc) and most preferably at least 184 days. With respect to the antibody detection assay, those of skill in the art will be able to identify and utilize appropriate products. ELISA assays and especially the IDEXX Herdchek *M. hyo* Test Kit™ (IDEXX Laboratories, Inc., Westbrook, Me.) are preferred.

In another aspect of the present invention, a method for eliciting a protective immune response against PCV2 in a pig is provided. Generally, the method comprises the step of administering an immunogenic composition in accordance with the present invention to an animal in need thereof, preferably a pig. Preferably, the immunogenic composition comprises porcine circovirus type 2 antigen and *M. hyo* antigen. Even more preferably, the amount of the PCV2 antigen in each dose has a relative potency (RP) value of at least 1.38, wherein an RP value of 1.38 for PCV2 means that at least 85% of mice receiving an administration of one-twentieth of such amount of PCV2 antigen develop a detectable amount of antibodies within or at 21 days post treatment in a PCV2 specific antibody detection assay. Preferably, an RP value of 1.38 for PCV2 means that at least 95% and preferably 100% of mice receiving an administration of one-tenth of such amount of PCV2 antigen develop a detectable amount of antibodies within or at 21 days post treatment in a PCV2 specific antibody detection assay. Consequently, the present invention also relates to method for eliciting a protective immune response in a pig against PCV2 comprising administering to said pig an immunogenic composition which comprises PCV2 antigen and *M. hyo* antigen, wherein the amount of the PCV2 antigen per dose has a relative potency value of at least 1.38, wherein said RP value of 1.38 corresponds to the 20-fold amount of PCV2 antigen that is needed to induce a detectable PCV2 specific antibody response in at least 85% of mice within or at 21 days post treatment. Preferably, said RP value of 1.38 corresponds to the 10-fold amount of PCV2 antigen that is needed to induce a detectable PCV2 specific antibody response in at least 95% and preferably 100% of mice within or at 21 days post treatment. In some preferred forms of this embodiment, the composition further includes or comprises an adjuvant. A variety of adjuvants will be useful with the present invention and can be selected by those of skill in the art, but carbomer and even more preferably CARBOPOL™ are particularly preferred. Advantageously, the immunogenic composition of the present invention elicits a protective immune response when administered to a pig as a single dose administration. Such a single dose elicits a duration of immunity of at least 100, more preferably at least 110, even more preferably at least 120, still more preferably at least 130, even more preferably at least 140, still more preferably at least 150, even more preferably at least 160, still more preferably at least 170, even more preferably at least 180, and most preferably at least 184 days when administered to a pig. In other words, one dose of the immunogenic composition of the present invention, without boosters or subsequent doses, provides an animal or group of animals with a reduced incidence of or lessened severity of clinical signs of infection from PCV2 for at least 100 (110, 120, 130, 140, 150, 160, 170, 180, etc) and most preferably for at least 184 days. With respect to the antibody detection assay, those of skill in the art will be able to identify and utilize appropriate methods and products. ELISA assays and the procedures described by Nawagitgul, P., et al. (the teachings and content of which are hereby incorporated by reference) in *Modified indirect porcine circovirus* (*PCV*) *type* 2*-based and recombinant capsid protein* (*ORF*2)*-based ELISA for the detection of antibodies to* PCV Diagn. Lab. Immunol. 9:33-40 (2002), are particularly preferred.

In yet another aspect of the present invention, a method for inducing or eliciting a protective immune response against *M. hyo* infection and PCV2 infection is provided. In preferred forms, this aspect includes an immunogenic composition comprising an effective amount of *M. hyo* antigen and an effective amount of PCV2 antigen. Preferably, both the *M. hyo* antigen and the PCV2 antigen will have an RP value of at least 1.22 and 1.38, respectively, as described above wherein an RP value of 1.22 for *M. hyo* and 1.38 for PCV2 means that 95% and preferably 100% of mice receiving an administration of one-fortieth of such amount of *M. hyo* and one-tenth of such amount of PCV2 antigen develop a detectable amount of antibodies within or at 21 days post treatment in an *M. hyo* and PCV2 specific antibody detection assay. Consequently, the present invention also relates to method for eliciting a protective immune response in a pig against *M. hyo* and PCV2 comprising administering to said pig an immunogenic composition which comprises PCV2 antigen and *M. hyo* antigen, wherein the amount of the *M. hyo* and PCV2 antigen per dose has a relative potency value of at least 1.22 and 1.38 respectively, wherein said RP value of 1.22 for the *M. hyo* antigen corresponds to the 40-fold amount of *M. hyo* antigen that is needed to induce a detectable *M. hyo* specific antibody response in at least 95% and preferably 100% of mice within or 21 days post treatment and wherein said RP value of 1.38 for the PCV2 antigen corresponds to the 20-fold amount of PCV2 antigen that is needed to induce a detectable PCV2 specific antibody response in at least 85% of mice within or 21 days post treatment. Preferably, said RP value of 1.38 for the PCV2 antigen corresponds to the 10-fold amount of PCV2 antigen that is needed to induce a detectable PCV2 specific antibody response in at least 95% and preferably 100% of mice within or 21 days post treatment. In some preferred forms of this embodiment, the composition further includes or comprises an adjuvant. A variety of adjuvants will be useful with the present invention and can be selected by those of skill in the art, but carbomer and especially CARBOPOL™ are particularly preferred. Advantageously, the immunogenic composition of the present invention elicits a protective immune response when administered to a pig as a single dose administration. Such a single dose elicits a duration of immunity of at least 100, more preferably at least 110, even more preferably at least 120, still more preferably at least 130, even more preferably at least 140, still more preferably at least 150, even more preferably at least 160, still more preferably at least 170, even more preferably at least 180, and most preferably at least 184 days when administered to a pig. In other words, one dose of the immunogenic composition of the present invention, without boosters or subsequent doses, provides an animal or group of animals with a reduced incidence of or lessened severity of clinical signs of infection from *M. hyo* and PCV2 for at least 100 (110, 120, 130, 140, 150, 160, 170, 180, etc) and most preferably at least 184 days. With respect to the antibody detection assay, those of skill in the art will be able to identify and utilize appropriate methods and products. ELISA assays and the procedures described by Nawagitgul, P., et al. (the teachings and content of which are hereby incorporated by reference) in *Modified indirect porcine circovirus* (*PCV*) *type* 2-*based and recombinant capsid protein* (*ORF*2)-*based ELISA for the detection of antibodies to PCV* Clin. Diagn. Lab. Immunol. 9:33-40 (2002), are particularly preferred for a PCV2 antibody detection assay and the IDEXX Herdchek *M hyo* Test Kit™ is particularly preferred for the *M. hyo* antibody detection assay.

As used herein, a "protective immune response" refers to a reduced incidence of or reduced severity of clinical, pathological, or histopathological signs of infection from *M. hyo* or PCV2 infection up to and including the complete prevention of such signs.

In another aspect of the present invention, a method for preparing a composition, preferably an antigenic or immunogenic composition, such as for example a vaccine, for invoking an immune response against PCV2 and *M. hyo* is provided. Generally, this method includes the steps of transfecting a construct into a virus, wherein the construct comprises i) recombinant DNA from ORF2 of PCV2, ii) infecting cells in growth media with the transfected virus, iii) causing the virus to express the recombinant protein from PCV2 ORF2, iv) recovering the expressed ORF2 protein from the supernate, v) and preparing the composition by combining the recovered protein with a suitable adjuvant and/or other pharmaceutically acceptable carrier, together with *M. hyo* bacterin and a suitable adjuvant. Due to the long-term stability of the components of the immunogenic composition, the composition can be administered to animals up to 3 years after being mixed together. Preferred forms of the composition described herein will have an *M. hyo* portion with an RP value greater than about 1.22, more preferably between about 1.22 to about 4.5, even more preferably between about 1.22 and 3.5, and most preferably between about 1.22 and 2.8. An RP value for *M. hyo* is greater than about 1.22 when 95% and more preferably 100% of mice treated with one-fortieth of the amount of *M. hyo* antigen associated with the RP value of 1.22 develop a detectable amount of antibodies against *M. hyo* using an *M. hyo*-specific antibody detection assay within or at 21 days post treatment or post administration of the *M. hyo* antigen.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid, which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL™; (BF Goodrich, Ohio, USA) are particularly appropriate. They are cross-linked with an allyl sucrose or with allyl pentaerythritol. Among then, there may be mentioned CARBOPOL 974P™, 934P and 971P. Most preferred is the use of CARBOPOL 971P™. Among the copolymers of maleic anhydride and alkenyl derivative, the copolymers EMA (Monsanto), which are copolymers of maleic anhydride and ethylene, are also contemplated. The dissolution of these polymers in water leads to an acid solution that will be neutralized, preferably to physiological pH, in order to give the adjuvant solution into which the immunogenic, immunological or vaccine composition itself will be incorporated. Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others.

Preferably, the adjuvant is added in an amount of about 100 μg to about 10 mg per dose. Even more preferably, the adjuvant is added in an amount of about 100 μg to about 10 mg per dose. Even more preferably, the adjuvant is added in an amount of about 500 μg to about 5 mg per dose. Even more preferably, the adjuvant is added in an amount of about 750 μg to about 2.5 mg per dose. Most preferably, the adjuvant is added in an amount of about 1 mg per dose.

Thus, according to a further aspect, the method for preparing an antigenic composition, such as for example a vaccine, for invoking an immune response against PCV2 and *M. hyo* comprises i) admixing PCV2 ORF2 protein with *M. hyo* bacterin and a suitable adjuvant. Preferably, the adjuvant is a carbomer, and more preferably is CARBOPOL 971P. Even more preferably, CARBOPOL 971P™ is added in an amount of about 500 μg to about 5 mg per dose, even more preferably in an amount of about 750 μg to about 2.5 mg per dose and most preferably in an amount of about 1 mg per dose.

Additionally, the vaccine composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like.

The immunogenic compositions can further include one or more other immunomodulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 μg to about 2000 μg of adjuvant and preferably about 250 μg/ml dose of the vaccine composition. In another preferred embodiment, the present invention contemplates vaccine compositions comprising from about 1 ug/ml to about 60 μg/ml of antibiotics, and more preferably less than about 30 μg/ml of antibiotics.

A "PCV2 antigen" refers to any composition of matter that comprises at least one antigen that can induce, stimulate or enhance the immune response against PCV2 infection, when administered to a pig. Preferably, said PCV2 antigen is the whole PCV2 virus, preferably in an inactivated form, a life modified or attenuated PCV2 virus, a chimeric virus that comprises at least an immunogenic amino acid sequence of PCV2, any other polypeptide or component that comprises at least an immunogenic amino acid sequence of PCV2. The terms "immunogenic protein", "immunogenic polypeptide" or "immunogenic amino acid sequence" as used herein refer to any amino acid sequence which elicits an immune response in a host against a pathogen comprising said immunogenic protein, immunogenic polypeptide or immunogenic amino acid sequence. An "immunogenic protein", "immunogenic polypeptide" or "immunogenic amino acid sequence" as used herein, includes the full-length sequence of any proteins, analogs thereof, or immunogenic fragments thereof. By "immunogenic fragment" is meant a fragment of a protein, which includes one or more epitopes and thus elicits the immunological response against the relevant pathogen. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes are readily identified by determining spatial conformation of amino acids such as by, e.g., x-ray crystallography and 2-dimensional nuclear magnetic resonance See, e.g., Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, June 28-Jul. 3, 1998.

Most preferably, the vaccine composition that can be used according to the invention contains PCV2 ORF2 protein, preferably expressed in and recovered from in vitro cultured cells. Preferred examples of PCV2 ORF2 proteins are described in the international patent application WO2006-072065, the teaching and content of which is entirely incorporated herein by reference.

Briefly, PCV2 ORF2 DNA and protein, as used herein for the preparation of the compositions and also as used within the processes provided herein is a highly conserved domain within PCV2 isolates and thereby, any PCV2 ORF2 would be effective as the source of the PCV2 ORF2 DNA and/or polypeptide as used herein. A preferred PCV2 ORF2 protein is that of SEQ ID NO. 11. A preferred PCV ORF2 polypeptide is provided herein as SEQ ID NO. 5, but it is understood by those of skill in the art that this sequence could vary by as much as 6-10% in sequence homology and still retain the antigenic characteristics that render it useful in immunogenic compositions. The antigenic characteristic of a modified antigen is still retained, when the modified antigen confers at least 70%, preferably 80%, and more preferably 90% of the protective immunity as compared to the PCV2 ORF 2 protein, encoded by the polynucleotide sequence of SEQ ID NO: 3 or SEQ ID NO: 4. An "immunogenic composition" as used herein, means a PCV2 ORF2 protein that elicits an "immunological response" in the host of a cellular and/or antibody-mediated immune response to PCV2 ORF2 protein. Preferably, this immunogenic composition is capable of conferring protective immunity against PCV2 infection and the clinical signs associated therewith. In some forms, immunogenic portions of PCV2 ORF2 protein are used as the antigenic component in the composition. The term "immunogenic portion" as used herein refers to truncated and/or substituted forms, or fragments of PCV2 ORF2 protein and/or polynucleotide, respectively. Preferably, such truncated and/or substituted forms, or fragments will comprise at least 6 contiguous amino acids from the full-length ORF2 polypeptide. More preferably, the truncated or substituted forms, or fragments will have at least 10, more preferably at least 15, and still more preferably at least 19 contiguous amino acids from the full-length ORF2 polypeptide. Two preferred sequences in this respect are provided herein as SEQ ID NOs. 9 and 10. It is further understood that such sequences may be a part of larger fragments or truncated forms. A further preferred PCV2 ORF2 polypeptide provided herein is encoded by the nucleotide sequences of SEQ ID NO: 3 or SEQ ID NO: 4. However, it is understood by those of skill in the art that this sequence could vary by as much as 6-20% in sequence homology and still retain the antigenic characteristics that render it useful in immunogenic compositions. In some forms, a truncated or substituted form, or fragment of ORF2 is used as the antigenic component in the composition. Preferably, such truncated or substituted forms, or fragments will comprise at least 18 contiguous nucleotides from the full-length ORF2 nucleotide sequence, e.g. of SEQ ID NO: 3 or SEQ ID NO: 4. More preferably, the truncated or substituted forms, or fragments will have at least 30, more preferably at least 45, and still more preferably at least 57 contiguous nucleotides the full-length ORF2 nucleotide sequence, e.g. of SEQ ID NO: 3 or SEQ ID NO: 4.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs that determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions that are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homologous sequence comprises at least a stretch of 50, even more preferably 100, even more preferably 250, even more preferably 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Preferably, said PCV2 ORF2 protein is i) a polypeptide comprising the sequence of SEQ ID NO: 5, SEQ ID NO: 6, SEQ ID NO: 9, SEQ ID NO: 10 or SEQ ID NO: 11;

ii) any polypeptide that is at least 80% homologous to the polypeptide of i), iii) any immunogenic portion of the polypeptides of i) and/or iv) the immunogenic portion of comprising at least 10 contiguous amino acids included in the sequences of SEQ ID NO: 5, SEQ ID NO: 6, SEQ ID NO: 9, SEQ ID NO: 10 or SEQ ID NO: 11, v) a polypeptide that is encoded by a DNA comprising the sequence of SEQ ID NO: 3 or SEQ ID NO: 4.

vi) any polypeptide that is encoded by a polynucleotide that is at least 80% homologous to the polynucleotide of v), vii) any immunogenic portion of the polypeptides encoded by the polynucleotide of v) and/or vi)

viii) the immunogenic portion of vii), wherein the polynucleotide coding for said immunogenic portion comprises at least 30 contiguous nucleotides included in the sequences of SEQ ID NO: 3, or SEQ ID NO: 4.

Preferably any of those immunogenic portions will have the immunogenic characteristics of PCV2 ORF2 protein that is encoded by the sequence of SEQ ID NO: 3 or SEQ ID NO: 4.

As mentioned above, the relative potency (RP) of the PCV2 ORF2 portion of the composition is at least 1.38, more preferably between about 1.38 and 4.5, still more preferably between about 1.38 and 3.5, even more preferably between about 1.38 and 3, and most preferably between about 1.38 and 2.75. Similar to the determination of an RP value of at least 1.22 with respect to *M. hyo*, an RP value for PCV2 is greater than about 1.38 when 85% of mice treated with one-twentieth of the amount of PCV2 antigen associated with an RP value of 1.38 develop a detectable amount of antibodies against PCV2 using a PCV2-specific antibody detection assay within or at 21 days post treatment or post administration of the PCV2 antigen. Preferably, an RP value for PCV2 is greater than about 1.38 when 95% and preferably 100% of mice treated with one-tenth of the amount of PCV2 antigen associated with an RP value of 1.38 develop a detectable amount of antibodies against PCV2 using a PCV2-specific antibody detection assay within or at 21 days post treatment or post administration of the PCV2 antigen.

The PCV2 ORF2 protein used in an immunogenic composition in accordance with the present invention can be derived in any fashion including isolation and purification of PCV2 ORF2, standard protein synthesis, and recombinant methodology. Preferred methods for obtaining PCV2 ORF2 polypeptide are also provided in the international patent application WO 2006-072065, which corresponds to the U.S. patent application Ser. No. 11/034,797, the teachings and content of which are hereby incorporated by reference.

According to further embodiment, said PCV2 antigen is INGELVAC®CIRCOFLEX, (Boehringer Ingelheim Vetmedica Inc, St Joseph, Mo., USA), CIRCOVAC® (Merial SAS, Lyon, France), CIRCOVENT (Intervet Inc., Millsboro, Del., USA), or SUVAXYN PCV-2 ONE DOSE® (Fort Dodge Animal Health, Kansas City, Kans., USA), or any of the PCV2 antigens included in any of the vaccines mentioned above. Most preferably, the PCV2 antigen is that which is included in INGELVAC®CIRCOFLEX or is INGELVAC®CIRCOFLEX.

A "*M. hyo* antigen" refers to any composition of matter that comprises at least one antigen that can induce, stimulate or enhance the immune response against *M. hyo* infection, when administered to a pig. Preferably, said *M. hyo* antigen is the whole *M. hyo* bacterin, preferably in an inactivated form, a live modified or attenuated *M. hyo* bacterium, a chimeric virus that comprises at least an immunogenic amino acid sequence of *M. hyo*, or any other polypeptide or component that comprises at least an immunogenic amino acid sequence of *M. hyo*. Preferably the *M. hyo* antigen is an inactivated *M. hyo* bacterin. More preferably the *M. hyo* antigen is derived from the *M. hyo* J-strain. Most preferably the *M. hyo* bacterin is the inactivated *M. hyo* bacterin that is included in INGELVAC®MYCOFLEX vaccine (Boehringer Ingelheim Vetmedica Inc, St Joseph, Mo., USA) or is INGELVAC® MYCOFLEX. However, the *M. hyo* antigen that can be used according to the invention can also selected from any one which is included in the following vaccine compositions: PORCILIS *M. HYO*, MYCO SILENCER® BPM, MYCO SILENCER® BPME, MYCO SILENCER® ME, MYCO SILENCER® M, MYCO SILENCER® ONCE, MYCO SILENCER® MEH (all of Intervet Inc., Millsboro, Del., USA) STELLAMUNE MYCOPLASMA™ (Pfizer Inc., New York, N.Y., USA), SUVAXYN MYCOPLASMA™, SUVAXYN *M. HYO*™, SUVAXYN MH-ONE™ (all of Fort Dodge Animal Health, Overland Park, Kans., USA (Wyeth).

Injection timing is flexible. Compositions as described herein can be used as early as three weeks of age through the time when pigs leave the nursery with the objective of vaccinating at least 2 weeks prior to exposure to *Mycoplasma hyopneumoniae*. The composition according to the invention may be applied in any conventional manner including intradermally, intratracheally, or intravaginally. The composition preferably may be applied intramuscularly or intranasally. In an animal body, it can prove advantageous to apply the pharmaceutical compositions as described above via an intravenous injection or by direct injection into target tissues. For systemic application, the intravenous, intravascular, intramuscular, intranasal, intra-arterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the invention may be administered once or several times, also intermittently, for instance on a daily basis for several days, weeks or months, and in different dosages. However, as detailed herein, the combination of *M. hyo* bacterin and PCV2 ORF 2 provides an immunogenic composition that provides effective immunity and/or reduces the severity of or incidence of clinical signs associated with *M. hyo* and/or PCV2 infection in pigs receiving such a composition after just one dose.

"Decrease" or "reduction in the incidence of or severity of clinical, pathological, and/or histopathological signs" shall mean that any of such signs are reduced in incidence or severity in animals receiving an administration of the vaccine in comparison with a "control group" of animals when both have been infected with or challenged by the pathogen from which the immunological active component(s) in the vaccine are derived and wherein the control group has not received an administration of the vaccine or immunogenic composition. In this context, the term "decrease" or "reduction" means a reduction of at least 10%, preferably 25%, even more preferably 50%, and most preferably of 100% in the vaccinated group as compared to the control group as defined above.

"Clinical signs" shall refer to signs of infection from a pathogen that are directly observable from a live animal such as symptoms. Representative examples will depend on the pathogen selected but can include things such as nasal discharge, lethargy, coughing, elevated fever, weight gain or loss, dehydration, diarrhea, swelling, lameness, and the like. PCV2 clinical signs can include wasting, paleness of the skin, unthriftiness, respiratory distress, diarrhea, icterus, and jaundice. Clinical signs of *M. hyo* infection include a dry cough, impaired performance, and lung lesions.

"Pathological" signs shall refer to signs of infection that are observable at the microscopic or molecular level, through biochemical testing, or with the naked eye upon necropsy. For PCV2, pathological signs will include microscopic and macroscopic lesions on multiple tissues and organs, with lymphoid organs being the most common site for lesions.

"Histopathological" signs shall refer to signs of tissue changes resulting from infection.

In another embodiment of the present invention *M. hyo* antigen, preferably *M. hyo* bacterin, is combined with antigen from another disease-causing organism in swine. In such cases, the RP value of the *M. hyo* portion is as described above. In another embodiment of the present invention, PCV2 antigen is combined with antigen from another disease-causing organism in swine. In such cases, the RP value of the PCV2 portion is as described above. Furthermore, in another embodiment of the present invention, PCV2 antigen and *M. hyo* antigen, preferably *M. hyo* bacterin, are combined with antigen from another disease-causing organism in swine. In such cases, the RP value of the *M. hyo* and PCV2 portion are as described above.

Preferably the other disease-causing organism in swine is selected from the group consisting of: *Actinobacillus* pleuropneumonia (1); Adenovirus (2); Alphavirus such as Eastern equine encephalomyelitis viruses (3); *Bordetella bronchiseptica* (4); *Brachyspira* spp. (5), preferably *B. hyodyentheriae* (6); *B. piosicoli* (7), *Brucella suis*, preferably biovars 1, 2, and 3 (8); Classical swine fever virus (9); *Clostridium* spp. (10), preferably *Cl. difficile* (11), *Cl. perfringens* types A, B, and C (12), *Cl. novyi* (13), *Cl. septicum* (14), *Cl. tetani* (15); Coronavirus (16), preferably Porcine Respiratory Corona virus (17); Eperythrozoonosis suis (18); *Erysipelothrix rhusiopathiae* (19) *Escherichia coli* (20); *Haemophilus parasuis*, preferably subtypes 1, 7 and 14 (21) Hemagglutinating encephalomyelitis virus (22); Japanese Encephalitis Virus (23); Lawsonia intracellularis (24) *Leptospira* spp. (25), preferably *Leptospira australis* (26); *Leptospira canicola* (27); *Leptospira grippotyphosa* (28); *Leptospira icterohaemorrhagicae* (29); and *Leptospira* interrogans (30); *Leptospira pomona* (31); *Leptospira tarassovi* (32); *Mycobacterium* spp. (33) preferably *M. avium* (34), *M. intracellulare* (35) and *M. bovis* (36); *Pasteurella multocida* (37); Porcine cytomegalovirus (38); Porcine Parvovirus (39); Porcine Reproductive and Respiratory Syndrome (PRRS) Virus (40) Pseudorabies virus (41); Rotavirus (42); *Salmonella* spp. (43), preferably *S. thyphimurium* (44) and *S. choleraesuis* (45); *Staph. hyicus* (46); *Staphylococcus* spp. (47) preferably *Streptococcus* spp. (48), preferably Strep. suis (49); Swine herpes virus (50); Swine Influenza Virus (51); Swine pox virus (52); Swine pox virus (53); Vesicular stomatitis virus (54); Virus of vesicular exanthema of swine (55); *Leptospira Hardjo* (56); Porcine circovirus (57); and/or *Mycoplasma hyosynoviae* (58).

Any reference made in connection with a swine pathogen in the following can be made by naming the pathogen, for example *Pasteurella multocida*, or by making reference to the number in ( ) behind the pathogen that is found above. For example reference to *Pasteurella multocida* can be made by *Pasteurella multocida* or by (37).

Thus, the present invention relates to a combination vaccine for the treatment and/or prophylaxis of swine, that includes an immunological agent effective for reducing the incidence of or lessening the severity of *M. hyo* and/or PCV2 infection(s), and further an immunological active component effective for the treatment and/or prophylaxis of infections caused by any of the swine pathogens (1), (2), (3), (4), (5), (6), (7), (8), (9), (10), (11), (12), (13), (14), (15), (16), (17), (18), (19), (20), (21), (22), (23), (24), (25), (26), (27), (28), (29), (30), (31), (32), (33), (34), (35), (36), (37), (38), (39), (40), (41), (42), (43), (44), (45), (46), (47), (48), (49), (50), (51), (52), (53), (54), (55), (56), (57) and/or (58), or is an immunological active component of said swine pathogen(s).

An "immunological active component" as used herein means a component that induces or stimulates the immune response in an animal to which said component is administered. According to a preferred embodiment, said immune response is directed to said component or to a microorganism comprising said component. According to a further preferred embodiment, the immunological active component is an attenuated microorganism, including modified live virus (MLV), a killed-microorganism or at least an immunological active part of a microorganism.

"Immunological active part of a microorganism" as used herein means a protein-, sugar-, and or glycoprotein containing fraction of a microorganism that comprises at least one antigen that induces or stimulates the immune response in an animal to which said component is administered. According to a preferred embodiment, said immune response is directed to said immunological active part of a microorganism or to a microorganism comprising said immunological active part.

According to further aspect, the further immunological active component of the combination vaccine is selected from the group consisting ENTERISOL® ILEITIS, ENTERISOL® ILEITIS FF, ENTERISOL® SC-54, ENTERISOL® SC-54 FF, ENTERISOL® ERY-ALC, INGELVAC® APP ALC, INGELVAC® AR4, INGELVAC® HP-1, INGELVAC® HPE-1, INGELVAC® PRRS MLV, INGELVAC® PRRS ATP, INGELVAC® PRV-G1, REPROCYC® PRRS PLE, REPROCYC® PLE, TETGUARD™, TOXIVAC® AD+E, TOXIVAC® PLUS PARASUIS, (all of Boehringer Ingelheim, St. Joseph, Mo., USA); CIRCOVENT, PORCILIS COLI, PORCILIS ERY+ PARVO, PORCILIS ERY, PORCILIS GLASSER, PORCILIS PARVO, PORCILIS PORCOLI DF, PORCILIS APP, PORCILIS AR-T, PORCILIS AR-T DF, PORCILIS PORCOLI, PORCILIS PORCOLI DILUVAC FORTE, PORCILIS PRRS, PORCILIS PORCOL 5, PORCILIS AUJESZKY, PORCILIS BEGONIA DILUVAC, PORCILIS BEGONIA I.D.A.L., PORCILIS BEGONIA UNISOLE, PORCILIS *M. HYO*, PORCILIS ATRINORD, RHINOGEN® BPE, RHINOGEN® CTE 5000, RHINOGEN® CTSE, SCORE, SOW BAC® E II, SOW BAC® CE II, SOW BAC® TREC, PROSYSTEM® CE, PROSYSTEM® RCE, PROSYSTEM® TREC, PROSYSTEM® PILLMUNE, PROSYSTEM® ROTAMUNE® with IMUGAN® II, PROSYSTEM® ROTA, PROSYSTEM® ROTAMUNE KV, PROSYSTEM® TG-EMUNE® ROTA with IMUGAN® II, PROSYSTEM® TGE/ROTA, PROSYSTEM® TG-EMUNE® with IMUGEN®, PROSYSTEM® TGE, MAGESTIC 7, MAGESTIC 8, MAGESTIC™ with SPUR®, MAGESTIC® 7 with SPUR®, MAGESTIC® 8 with SPUR®, END-FLUENCE® with IMUGEN® II, END-FLUENCE® 2, PRROMISE®, PRV-BEGONIA with DILUVAC FORTE®, ARGUS® SC/ST, STREP BAC, STREP BAC® with IMUGEN® II, COLISORB, HEPTA-VAC, LAMBIVAC, PORCOVAC PLUS, ERYSORB PARVO all of Intervet Inc., Millsboro, Del., USA); HYO-RESP, CIRCOVAC, NEOCOLIPOR, PARVORUVAC, PARVOSUIN, PROGRESSIS, VIRAFLU, AKIPOR 6.3, JESPUR GL-, JESFLU GL—(all of Merial LTD, Duluth, Ga.); ER BAC® PLUS, ER BAC®, ER BAC® PLUS/LEPTOFERM-5® ER BAC® LEPTOFERM-5®, FARROWSURE®, FARROWSURE® B, FARROWSURE® PLUS B, FARROWSURE® PLUS, FARROWSURE® PRV, FARROWSURE B-PRV, FLUSURE™, FLUSURE™ RTU, FLUSURE™/ER BAC® PLUS, FLUSURE™/ER BAC PLus®, FLUSURE™/RESPISURE®, FLUSURE™/RESPISURE® RTU, FLUSURE™/RESPISURE-ONE®/ER BAC® PLUS, FLUSURE™/RESPISURE 1 ONE®/ER BAC PLUS®, FLUSURE™/RESPISURE ONE®, FLUSURE™/RESPISURE 1 ONE®, FLUSURE/FARROWSURE PLUS, FLUSURE/FARROWSURE PLUS B, LITTERGUARD® LT-C, LITTERGUARD® LT, PLEUROGUARD® 4, PNEUMOSUIS III, STELLAMUNE ONE, STELLAMUNE UNO, STELLAMUNE ONCE, STELLAMUNE MONO, RESPISURE ONE, RESPISURE®, RESPISURE 1 ONE®, RESPISURE 1 ONE®/ER BAC PLUS®, ENDURACELL T, ZYLEXIS (formerly known as Baypamune), ATROBAC® 3, BRATIVAC®, BRATIVAC®-B, LEPTOFERM-5°°-PARVOVAC®/LEPTOFERM-5®, PR-VAC®-Killed, PR-VAC, PR-VAC PLUS™ (all of Pfizer Inc., New York, N.Y., USA); SUVAXYN MH ONE, SUVAXYN RESPIFEND® MH, SUVAXYN AUJESZKY BARTHA+DILUENT, SUVAXYN AUJESZKY BARTHA+O/W, SUVAXYN AUJESZKY-FLU, SUVAXYN AUJESZKY 783+O/W, SUVAXYN ERY, SUVAXYN FLU, *M. HYO* SUVAXYN PARVO ST, SUVAXYN PARVO/E, SUVAXYN RESPIFEND® APP, SUVAXYN RESPIFEND® HPS, SUVAXYN RESPIFEND® MH/HPS, SUVAXYN RESPIFEND® MH, SUVAXYN® AR/T/E, SUVAXYN® EC-4, SUVAXYN® E, SUVAXYN®-E, SUVAXYN® E-ORAL, SUVAXYN® PLE, SUVAXYN® PLE/PrV GPL-, SUVAXYN® LE+B, SUVAXYN® PLE+B, SUVAXYN® PLE+B/PrV GPL-, SUVAXYN® SIV, SUVAXYN® SIV/MH-ONE, SUVAXYN® P, SUVAXYN® PrV GPL-, SUVAXYN® PCV-2 ONE SHOT (all of Fort Dodge Animal Health, Overland Park, Kans., USA (Wyeth); SCOURMUNE®, SCOURMUNE®-C, SCOURMUNE®-CR, AR-PAC®-PD+ER, AR-PARA-PAC®+ER, M+RHUSIGEN®, M+PAC®, MAXIVAC EXCELL®3, MAXIVAC® H1N1, MAXIVAC® H3N2, MAXIVAC®-FLU, MAXIVAC®-M+, MAXIVAC EXCELL®, MAXIVAC EXCELL 3, PARAPAC®, PNEU PAC®, PNEU PAC®-ER, PNEU PAC®+ER, PRV/MARKER GOLD®, PRV/MARKER GOLD®, PRV/MARKER GOLD®-MAXIVAC® FLU, RHUSIGEN™, GLETVAX 6, COVEXIN 8, M+PAC, GLETVAX PLUS, M-PARAPAEL™ SS PAC® (all of Schering-Plough Animal Health Corporation, Kenilworth, N.J., USA); AMERVAC-PRRS, AUSKIPRA-BK, AUSKIPRA-GN, COLISUIN-CL, COLISUIN-TP, ERYSIPRAVAC, GRIPORK, HIPRASUIS-GLASSER, MYPRAVAC SUIS, NEUMOSUIN, PARVOSUIN, PARVOSUIN-MR, PARVOSUIN-MR/AD, RINIPRAVAC-DT, SUIPRAVAC-PRRS, SUIPRAVAC-RC, TOXIPRA PLUS (all of Laboratorios Hipra S.A., Amer, Girona, Spain); CLOSTRICOL, COLIPORC PLUS, HAEPPOVAE, PER-C-PORC, PORCIPARVAE, RESPIPORC ART+EP, RESPIPORC FLU, RESPIPORC *M. HYO* 1 SHOT, RHUSIOVAE, ROTLAUF-LEBENDIMPFSTOFF, SALMOPORC, SUISALORAL, AK-VAC MK35 (all of IDT Impfstoffwerk DessaTornau, Tornau, Germany); MYPRAVAE SUIS, (Albrecht GmbH, Germany); HAEMO SHIELD® P, PARAPLEURO SHIELD® P, PARAPLEURO SHIELD® P+BE, RHINICELL® ED, RHINI SHIELD™ TX4, PREFARROW SHIELD® 9, PREFARROW STREP SHIELD®, CLOSTRATOX® BCD, CLOSTRATOX® C, CLOSTRATOX® ULTRA C 1300, PORCINE ECOLIZER® 3+C, PORCINE PILI SHIELD™ C, PORCINE PILI SHIELD™PORCINE ECOLIZER® 3, ERY SERUM™ERY SHIELD™ERY VAC ORAL, ERY SHIELD™+L5, PANSTAR™ ERY, ERYCELL™PARVO SHIELD® E, PARVO SHIELD® L5E, PARVO SHIELD® L5, PARVO SHIELD®, PARVO SHIELD®, PNEUMOSTAR SIV, PNEUMOSTAR™ MYCO, LEPTO SHIELD™ 5, MYCO SHIELD™SALMOSHIELD® 2, SALMO SHIELD® LIVE, AMITOX TET™C. PERFRINGENS TYPE A TOXOID (all of Novartis Animal Health, Basel, Switzerland); NITRO-SAL (Akro); or any antigen included in the compositions described above.

DETAILED DESCRIPTION OF THE PREFERRED EMBODIMENTS

The following examples set forth preferred materials and procedures in accordance with the present invention. It is to be understood, however, that these examples are provided by way of illustration only, and nothing therein should be deemed a limitation upon the overall scope of the invention.

Example 1

The study design was set up to evaluate the combination efficacy of PCV2-*M. hyo* at full and 2×½ dose, at two different inclusion levels of *M. hyo* for the combination product and also to demonstrate any interference of the combination product compared to the monovalent *M. hyo.*

Materials and Methods:

Pigs were divided into 6 groups. All of the challenge groups (Groups 1-5) had around 19 pigs in each group. The control group containing pigs that were not given treatment and were not challenged (Group 6) had 5 pigs in the group. All pigs were necropsied on Day 61 of the study. The Schedule of the Investigation is shown below in Table 1

TABLE 1

| Study Day (approximately) | Study Event |
|---|---|
| Before Day 0 (D0) | ID pigs; Health examination |
| Before D0 | Randomize pigs to one of five groups |
| D-2 | All pigs: Collect blood samples; Clinical Assessments |
| D0 | All pigs: Clinical Assessments |
| D0 | Administer Investigational Veterinary Product 1 (IVP1) to Group 1; Administer Investigational Veterinary Product 2 (IVP2) to Group 2; Administer Investigational Veterinary Product 3 (IVP3) to Group 3; Administer Investigational Veterinary Product 3 (IVP3) to Group 4; Administer Control Product (CP) to Group 5. |
| D1 to D33 | All pigs: Clinical Assessments |
| D12 | Collect blood samples from all animals. Administer IVP-3 to Group 3; CP administered to Group 5. |
| D32 | Move at least the strict control group (Group 6) to a separate room |

TABLE 1-continued

| Study Day (approximately) | Study Event |
|---|---|
| D33 | All pigs: Collect blood samples |
| | All pigs: Anesthetize; Challenge with virulent *M. hyopneumoniae* strain 232 |
| D32 to D63 | All pigs: Daily clinical observations |
| D47 | All pigs: Collect blood samples |
| D61 | All pigs: Collect blood samples |
| | All pigs: Euthanize; Necropsy; Score lungs; Collect lung samples |

This is a vaccination-challenge efficacy study conducted in a minimum of 100 piglets, approximately 21±6 days of age on Day 0 (D0).

Prior to the start of the study, piglets' sera was drawn and screened for serological status to *M. hyopneumoniae* and Porcine Reproductive and Respiratory Syndrome virus (PRRSV). Only piglets that were negative for *M. hyopneumoniae* and PRRSV antibodies in serum were considered for the study. Table 2 gives a summary of the study.

TABLE 2

| Group | Number | Treatment on D0 | Treatment on D12 | Challenge with *M. hyopneumoniae* On D33 | Day of Necropsy |
|---|---|---|---|---|---|
| 1 | ≥19 | 1.0 mL of IVP-1 (50 mL of *M. hyo* Bacterin) IM in the neck region | N/A | Yes | D61 |
| 2 | ≥19 | 2.0 mL of IVP-2 (100 mL: 50 mL of *M. hyo* Bacterin and 50 mL of PCV2 vaccine) IM in the neck region | N/A | Yes | D61 |
| 3 | ≥19 | 1.0 mL of IVP-3 (100 mL: 50 mL of *M. hyo* Bacterin and 50 mL of PCV2 vaccine) IM in the neck region | 1.0 mL of IVP-3 (100 mL: 50 mL of *M. hyo* Bacterin and 50 mL of PCV2 vaccine) IM in the neck region | Yes | D61 |
| 4 | ≥19 | 2.0 mL of IVP-3 (100 mL: 50 mL of *M. hyo* Bacterin and 50 mL of PCV2 vaccine) IM in the neck region | N/A | Yes | D61 |
| 5 | ≥19 | 2.0 mL of CP (50 mL saline) IM in the neck region | 1.0 mL of CP (50 mL saline) IM in the neck region | Yes | D61 |
| 6 | ≥5 | N/A | N/A | N/A | D61 |

IVP-1 (monovalent *M. hyo*) was serial 273-011B that had a release RP of 1.44 and an RP of 1.22 at 18 months. IVP-2 (PCV2-*M. hyo*) utilized *M. hyo* serial 273-011B (RP of 1.22 at 18 months) and PCV2 serial 309-035 (release RP of 1.38) IVP-3 (PCV2-*M. hyo*) was composed of *M. hyo* serial 273-010B (release RP 2.8) and PCV2 serial 309-035 (release RP of 1.38)

Prior to D0, all pigs were assigned completely at random to one of six groups. Group 1 consisted of ≥19 pigs and was assigned to the *M. hyo* vaccine treatment group (Investigational Veterinary Product-1 (IVP-1)) treated group. Group 2 consisted of ≥19 pigs and was assigned to a *M. hyo*-PCV2 vaccine (Investigational Veterinary Product-2 (IVP-2)) treatment group and was administered a 1×2.0 mL dose on day 0. Group 3 consisted of ≥19 pigs and was assigned to a *M. hyo*-PCV2 vaccine treatment group (IVP-3) and was administered a 1.0 mL dose on days 0 & 12. Group 4 consisted of ≥19 pigs and received a *M. hyo*-PCV2 vaccine (IVP-3) 1×2.0 mL on Day 0. Group 5 served as challenge controls and received 2.0 mL of control product on Day 0 and 1.0 mL of control product on Day 12. Group 6 served as strict controls and did not receive any product. Prior to D0, each pig was examined for overall health and had their blood sampled.

On D0, 1) ≥19 piglets assigned to Group 1 received 1.0 mL of IVP-1 IM; 2) ≥19 piglets assigned to Group 2 received 2.0 mL of IVP-2 IM; 3) ≥19 piglets assigned to Group 3 received 1.0 mL of IVP-3 IM on days 0 &12; 4) ≥19 piglets assigned to Group 4 received 2.0 mL of IVP-3 IM on Day 0; 5) ≥19 piglets assigned to Group 5 received 2.0 mL of CP IM on Study Day 0 and 1.0 mL IM on Study Day 12; and, 6) ≥5 piglets assigned to Group 6 did not receive product and served as strict controls.

On Study Day 0, treatments were administered in the right neck region, midway between the base of the ear and the point of the shoulder. On Study Day 12, treatment was administered in the left neck region, midway between the base of the ear and the point of the shoulder. All piglets were observed daily from D1 to D33 for any adverse events and overall health. All piglets were blood sampled on D33. On D33, each pig was challenged intratracheally with 10 ml of virulent *M. hyopneumoniae*. All pigs were observed daily for any clinical signs of disease from D32 to D61. Blood samples were collected from all pigs on D47 and D61. Blood samples collected prior to IVP administration were tested for *M. hyopneumoniae* and PRRS serology. Blood samples collected on D12, D33, D47 and D61 were tested for *M. hyopneumoniae* serology only. On D61, all pigs were euthanized and necropsied. The lungs and trachea were removed and the lungs scored. A sample was removed from each lung and tested by PCR for *M. hyopneumoniae* DNA. To determine if the study objective was achieved, lung lesion score data from Group 1, 2, 3 and 4 was compared to controls (Group 5) for statistically significant differences. Data from Group 6 was not included in any statistical analysis and was for information purposes only. Other *M. hyopneumoniae* parameters that were analyzed between Group 1, 2, 3 and 4 and controls (Group 5) included *M. hyopneumoniae* serology, post-vaccination clinical assessments and post-challenge clinical signs. PCR testing for the presence of *M. hyopneumoniae* DNA was completed on samples taken from the lungs to demonstrate an effective challenge.

Results and Discussion:

Upon necropsy, lungs were scored. One animal in Group 1 had consolidation and multiple abscesses and one animal in Group two had consolidation plus pleuritis. Statistical analysis was performed both with and without these two animals. As shown below, Group 3 had the lowest lung score of the vaccinated groups, with a score of 2.20. Group 4 had the highest lung score of the vaccinated groups, with a score of 4.19. Both Groups 1 and 2 had a lower lung score when animals 729 and 712, respectively, had been removed, with lung score for Group 1 being 2.13 and 2.56 for Group 2 with the animals removed. Lung scores for all of the vaccinated groups were significantly lower than the lung score of Group 5 (14.27) in which the pigs were challenged and no vaccine was administered.

Lung Scores:

| Group | Average Lung Scores |
|---|---|
| 1 | 5.54 |
| 1 (with 729 removed) | 2.13 |
| 2 | 3.90 |
| 2 (with 712 removed) | 2.56 |
| 3 | 2.20 |
| 4 | 4.19 |
| 5 | 14.27 |
| 6 | 0.00 |

Below is the statistical pairwise comparison summary. This includes analysis both with and without the two animals with conflicting factors.

Results of Pairwise Test-Scores.

| Comparison (Group v. Group) | Wilcoxon Two-Sample Test | P Value Median Two-Sample Test | P Value Two-Sample T Test |
|---|---|---|---|
| 1 vs. 5 | <0.0001 | <0.0001 | <0.0001 |
| 1 vs. 5 (729 Removed) | <0.0001 | <0.0001 | <0.0001 |
| 2 vs. 5 | <0.0001 | <0.0001 | <0.0001 |
| 2 vs. 5 (712 Removed) | <0.0001 | <0.0001 | <0.0001 |
| 3 vs. 5 | <0.0001 | <0.0001 | <0.0001 |
| 4 vs. 5 | <0.0001 | <0.0001 | <0.0001 |
| 1 vs. 2 | 0.3707 | 0.3872 | 0.3012 |
| 1 vs. 2 (712 and 729 Removed) | 0.1636 | 0.2931 | 0.1139 |
| 3 vs. 4 | 0.0006 | 0.0005 | 0.0165 |
| 2 vs. 4 | 0.2196 | 0.2706 | .7767 |
| 2 vs. 4 (712 Removed) | 0.1045 | 0.1511 | 0.5296 |
| 1 vs. 3 | 0.1752 | 0.1365 | 0.0247 |
| 1 vs. 3 (729 Removed) | 0.6212 | 0.3629 | 0.9196 |
| 1 vs. 4 | 0.0356 | 0.0515 | 0.3785 |
| 1 vs. 4 (729 Removed) | 0.0022 | 0.0135 | 0.0150 |

All vaccinated groups showed statistically significant results when compared to controls. There were differences between the 2×½ dose and the 1×2 ml dose (Groups 3 and 4). These groups had lung scores of 2.2 and 4.19 respectively. There were also differences between the monovalent and the high *M. hyo* antigen inclusion combo group (Group 1 versus 4). The results of this study provide surprising results that *M. hyo* in combination with PCV2 can provide an immunogenic effect when administered to pigs, as well as preserve the efficacy of the *M. hyo* component. Additionally, the results show that a single dose of the composition provides quick, long-lasting immunity. A single dose of this kind requires less time and manual labor and puts less stress on the pigs.

Example 2

This study design was set up to determine the duration of immunity of the combination vaccine.

Materials and Methods:

Pigs were divided into 6 groups. All of the challenge groups (Groups 1-5) had around 19 pigs in each group. The control group containing pigs that were not given treatment and were not challenged (Group 6) had 5 pigs in the group. The Schedule of the Investigation is shown below in Table 3.

TABLE 3

| Group | Number | Treatment on D0 | Treatment on D12 | Challenge with *M. hyopneumoniae* On D33 |
|---|---|---|---|---|
| 1 | ≥19 | 1.0 mL of IVP-1 (50 mL of *M. hyo* Bacterin) IM in the neck region | N/A | Yes |
| 2 | ≥19 | 2.0 mL of IVP-2 (100 mL: 50 mL of *M. hyo* Bacterin and 50 mL of PCV2 vaccine) IM in the neck region | N/A | Yes |
| 3 | ≥19 | 1.0 mL of IVP-3 (100 mL: 50 mL of *M. hyo* Bacterin and 50 mL of PCV2 vaccine) IM in the neck region | 1.0 mL of IVP-3 (100 mL: 50 mL of *M. hyo* Bacterin and 50 mL of PCV2 vaccine) IM in the neck region | Yes |
| 4 | ≥19 | 2.0 mL of IVP-3 (100 mL: 50 mL of *M. hyo* Bacterin and 50 mL of PCV2 vaccine) IM in the neck region | N/A | Yes |
| 5 | ≥19 | 2.0 mL of CP (50 mL saline) IM in the neck region | 1.0 mL of CP (50 mL saline) IM in the neck region | Yes |
| 6 | ≥5 | N/A | N/A | N/A |

The pigs in the challenged groups were challenged on D184 of the study. All piglets were observed daily from D1 to D33 for any adverse events and overall health. All piglets were blood sampled on D33. On D184, each pig was challenged intratracheally with 10 ml of virulent *M. hyopneumoniae*. All pigs were observed daily for any clinical signs of disease from D32 to D184. Blood samples were collected from all pigs on D47 and D61. Blood samples collected prior to IVP administration were tested for *M. hyopneumoniae* and PRRS serology. On D184, all pigs were euthanized and necropsied. The lungs and trachea were removed and the lungs scored.

Results and Discussion

After the pigs were necropsied their lungs were removed, and the lungs were observed for lung lesions. The vaccinated groups (Groups 1-4) had an average gross lung pathology of 6.2% (P>0.0023), the challenge control group (Group 5) had an average gross lung pathology of 14.9%, and the strict controls group (Group 6) had an average gross lung pathology of 1.6%. These results are summarized in Table 4 below.

TABLE 4

Efficacy of INGELVAC MYCOFLEX 26 weeks post-vaccination

| Treatment Group | Average Gross Lung Pathology (% of lung) |
|---|---|
| INGELVAC MYCOFLEX | 6.2% (P < 0.0023) |
| Challenge Controls | 14.9% |
| Strict Controls | 1.6% |

The results of this study indicate that the vaccine combination of *M. hyo* and PCV2 has a long-lasting effect in pigs that is at least 184 days or 26 weeks post vaccination. This is a surprising result given that the combination of *M. hyo* and PCV2 antigens is a novel combination.

Example 3

This investigation was carried out to determine the amount of interference observed when mixing an antigen of *M. hyo* with an antigen of PCV2. The study demonstrated that the *M. hyo* component of the vaccine was still effective in the presence of PCV2.

Materials and Methods

Pigs were 3 weeks±5 days of age at vaccination. Group 1 was vaccinated with a single 2 ml dose of *M. hyo* antigen in the form of a bacterin. Group 2 was vaccinated with a single 2 ml dose of equal amounts of *M. hyo* antigen and PCV2 antigen. Group 3 was a challenge control group and Group 4 was a strict control group. Groups 1-3 were subsequently challenged on D33 with a virulent *M. hyo* isolate. All animals in the study were necropsied at D61.

Results and Discussion

Upon necropsy, lungs were scored. Group 1, vaccinated with *M. hyo* antigen, only had average gross lung pathology of 5.5% (P>0.001). Group 2, vaccinated with *M. hyo* antigen and PCV2 antigen, had average gross lung pathology of 3.9% (P>0.001). Group 3, the challenge controls, had average gross lung pathology of 14.3% and Group 4, strict controls, had an average gross lung pathology of 0. The results are summarized below in Table 5.

TABLE 5

Efficacy of Ingelvac MycoFLEX as a monovalent and after mixing with CircoFLEX

| Treatment Group | Average Gross Lung Pathology (% of lung) |
|---|---|
| Ingelvac MycoFLEX | 5.5% (P < 0.001) |
| MycoFLEX mixed with CircoFLEX | 3.9% (P < 0.001) |
| Challenge Controls | 14.3% |
| Strict Controls | 0 |

The results of this study show that the difference in lung pathology, between those pigs vaccinated with *M. hyo* antigen alone versus those pigs vaccinated with a combination of *M. hyo* and PCV2 antigens, was not statistically significant. Therefore, this study shows that surprisingly, PCV2 antigen does not interfere with the immunogenic effect of the *M. hyo* antigen component. This makes the combination vaccine comprising *M. hyo* antigen and PCV2 antigen efficacious for infection by *M. hyo*. Additionally, it shows that this novel combination of antigens can be mixed and still provide the necessary protection against these pathogens after a single dose.

Example 4

This investigation was carried out to determine the efficacy of the composition, comprised of *M. hyo* antigen and PCV2 antigen, when challenged with PCV2.

Materials and Methods

The PCV2 efficacy evaluation was performed in sixty caesarian-derived, colostrum-deprived piglets. At approximately three weeks of age, piglets were vaccinated with INGELVAC® MYCOFLEX™, INGELVAC® PRRS MLV™ and INGELVAC® CIRCOFLEX™ in a single 2 ml dose. On day 31 post vaccination, vaccinate and control animals were administered a virulent PCV2 challenge virus. Twenty-two days following the administration of the challenge material, all animals were euthanized and the select tissues were removed and submitted for histology and immunohistochemistry (IHC) for PCV2. All procedures for handling and housing the piglets were observed as described in Example 1.

Results and Discussion

The criteria for the PCV2 efficacy evaluation were lymphoid depletion, lymphoid inflammation, and lymphoid IHC. The vaccinated group had 0% lymphoid depletion, 4.2% (1/24) lymphoid inflammation, and 8.3% (2/24) lymphoid IHC. The control group had 83.3% (20/24) lymphoid depletion, 87.5% (21/24) lymphoid inflammation, and 91.7% (22/24) lymphoid IHC. The results are summarized below in Table 6.

TABLE 6

Summary of PCV2 Primary Challenge Results

| Treatment | Lymphoid depletion +/total (%) | Lymphoid inflammation +/total (%) | Lymphoid IHC +/total (%) |
|---|---|---|---|
| Vaccine | 0/24 (0.0%) | 1/24 (4.2%) | 2/24 (8.3%)_ |
| Controls | 20/24 (83.3%) | 21/24 (87.5%) | 22/24 (91.7%) |
| P-value between groups | <0.0001 | <0.0001 | <0.0001 |

There were no injection site or other adverse reactions that could be attributed to the vaccine mixture.

The results, together with the results of the *M. hyo* challenge study described in Example 1, demonstrate that the mixture of *M. hyo* antigen and PCV2 antigen delivered in a single 2 ml dose is efficacious against infections by *M. hyo* and PCV2. The ability to mix these antigens provides needed protection against the pathogens *M. hyo* and PCV2 as well as decreasing the number of injection sites and subsequent stress on the animal while decreasing the labor required to administer two separate vaccines without sacrificing the safety of the individual vaccines. Further this demonstrates that the vaccine combination is efficacious for infection against PCV2.

Example 5

This example determined the number of mice producing detectable levels of antibodies to *M. hyo* or PCV2 after receiving an administration of an immunogenic composition comprising *M. hyo* antigen or PCV2 antigen in accordance with the present invention.

Materials and Methods

Antibody production was measured in mice from 5 different treatment groups, each having 20 mice therein. The first group received a dose of *M. hyo* antigen, the second and third groups received a dose of PCV2 antigen, and the last two groups served as a control group and received a dose of physiological saline and CARBOPOL™. Each mouse in Group 1 received a 0.1 ml administration of IVP-1 (monovalent *M. hyo* antigen) from serial 273-011B that had a release RP of 1.44 and an RP of 1.22 at 18 months (see Example 1 above). Prior to administration, the *M. hyo* antigen for each dose in Group 1 was diluted 1:4. Thus, the amount of antigen administered to the mice was 40-fold less than the amount of antigen administered to pigs in Example 1. Each mouse in Group 2 received a 0.2 ml administration of PCV2 antigen serial 309-035 (release RP of 1.38) (See Example 1 above). Similar to the *M. hyo* antigen for Group 1, the PCV2 antigen for each dose of Group 2 was diluted 1:2 with physiological saline such that it contained one-tenth of the PCV2 antigen administered to the pigs in Example 1 above. Each mouse in Group 3 received a 0.2 ml administration of PCV2 antigen serial 309-035 (release RP of 1.38) that had been diluted 1:4 with physiological saline such that it contained one-twentieth of the PCV2 antigen administered to the pigs in Example 1 above. Groups 4 and 5 each received a 0.1 ml (Group 4) or 0.2 ml (Group 5) administration of physiological saline/CARBOPOL™. After 21 days, antibody production was measured using a specific *M Hyo* antibody detection assay (ELISA) for Groups 1 and 4, and using a specific PCV2 antibody detection assay (ELISA) for groups 2, 3, and 5. If detectable amounts of antibodies were found using the assay, the result was termed "positive". If detectable amounts of antibodies were not found using the assay, the result was termed "negative."

Results

All mice in Group 1 were found to have detectable levels of *M. hyo* antibodies and all mice in Group 2 were found to have detectable levels of PCV2 antibodies 21 days after administration of the antigen-containing composition. In contrast, no detectable levels of *M. hyo* antibodies were found in Group 4 and no detectable levels of PCV2 antibodies were found in Group 5 21 days after administration of the physiological saline/CARBOPOL™ composition. Thus, one-fortieth of the antigen effective at inducing a protective immune response in pigs was able to produce detectable amounts of antibodies to *M. hyo* in 100% of mice receiving an administration of a composition in accordance with the present invention. This amount was defined as an RP of 1.22 for *M. hyo*. Moreover, one-tenth of the antigen effective at inducing a protective immune response in pigs was able to produce detectable amounts of antibodies to PCV2 in 100% of mice receiving an administration of a composition in accordance with the present invention. This amount was defined as an RP of 1.38 for PCV2.

The invention claimed is:

1. A method for eliciting a protective immune response in a pig against *Mycoplasma hyopneumoniae* (*M. hyo*) comprising administering to said pig a single dose of an immunogenic composition which comprises porcine circovirus type 2 antigen and *M. hyo* antigen, wherein the amount of the *M. hyo* antigen per a single dose is equivalent to 40-fold the amount of a determined relative potency value in mice, wherein the relative potency value in mice for *M. hyo* is determined by the steps:

(a) making serial dilutions of a composition containing an unknown amount *M. hyo* antigen to be determined to form a plurality of serial dilution groups with each member of each group having the same serial dilution;

(b) dividing a plurality of mice into groups to form a number of mice groups, wherein the number of mice groups is the same as the number of serial dilution groups and each mice group contains a plurality of mice;

(c) administering a single dose of each serial dilution group containing said *M. hyo* antigen of step (a) to each mouse in a mice group such that each mouse in a mice group receives the same serial dilution and each mice group receives a different serial dilution;

(d) taking a biological sample from each mouse in each mice group for each serial dilution group after a period of 21 days;

(e) detecting *M. hyo* specific antibodies present in the biological samples of step (d);

(f) determining the relative potency value of the *M. hyo* composition, wherein the relative potency is equal to the maximal serial dilution at which 100% of mice receiving said single dose of *M. hyo* antigen of step (c) develop a detectable amount of *M. hyo* antibodies within 21 days post treatment as detected in an *M. hyo* specific antibody detection assay of step (e);

(g) calculating the amount of *M. hyo* antigen to administer to a pig by multiplying the maximal serial dilution amount as determined in step (e) by a factor of 40; and (h) administering to said pig an immunogenic composition which comprises porcine circovirus type 2 antigen and *M. hyo* antigen, wherein the amount of the *M. hyo* antigen per a single dose is equivalent to the calculation of step (g).

2. The method of claim 1, wherein the amount of porcine circovirus type 2 antigen per a single dose is equivalent to 10-fold the amount of a determined relative potency (RP) value in mice, wherein the RP value in mice for porcine circovirus type 2 antigen is determined by the steps:

(a) making serial dilutions of a composition containing an unknown amount porcine circovirus type 2 antigen to be determined to form a plurality of serial dilution groups with each member of each group having the same serial dilution;

(b) dividing a plurality of mice into groups to form a number of mice groups, wherein the number of mice groups is the same as the number of serial dilution groups and each mice group contains a plurality of mice;

(c) administering a single dose of each serial dilution group containing said porcine circovirus type 2 antigen of step (a) each mouse in a mice group such that each mouse in a mice group receives the same serial dilution and each mice group receives a different serial dilution;

(d) taking a biological sample from each mouse in each mice group for each serial dilution group of step (c) after a period of 21 days;

(e) detecting porcine circovirus type 2 specific antibodies present in the biological samples of step (d);

(f) determining the relative potency value of the porcine circovirus type 2 composition, wherein the relative potency is equal to the maximal serial dilution at which 100% of mice receiving said single dose of porcine circovirus type 2 antigen of step (c) develop a detectable amount of porcine circovirus type 2 antibodies within 21 days post treatment as detected in a porcine circovirus type 2 specific antibody detection assay of step (e);

(g) calculating the amount of porcine circovirus type 2 antigen to administer to a pig by multiplying the maximal serial dilution amount as determined in step (f) by a factor of 10; and (h) administering to said pig the immunogenic composition which comprises porcine circovirus type 2 antigen and *M. hyo* antigen, wherein the amount of the porcine circovirus type 2 antigen per a single dose is equivalent to the calculation of step (g).

3. The method according to claim 1, wherein said immunogenic composition further comprises an adjuvant.

4. The method composition according to claim 3, wherein the adjuvant is a carbomer.

5. The method according to claim 1, wherein said immunogenic composition elicits a protective immune response against *M. hyo* when administered to said pig as a single dose administration.

6. The method according to claim 1, wherein said immunogenic composition elicits a protective immune response against *M. hyo* and porcine circovirus type 2 when administered to said pig as a single dose administration.

7. The method according to claim 1, wherein the immunogenic composition elicits a duration of immunity against *M. hyo* and/or porcine circovirus type 2 of at least 130 days when administered to said pig.

8. The method according to claim 7, wherein the immunogenic composition elicits a duration of immunity against *M. hyo* and/or porcine circovirus type 2 of at least 150 days when administered to said pig.

9. The method according to claim 7, wherein the immunogenic composition elicits a duration of immunity against *M. hyo* and/or porcine circovirus type 2 of at least 184 days when administered to said pig.

10. The method according to claim 1, wherein the specific antibody detection assay is an ELISA.

11. The method according to claim 2, wherein the specific antibody detection assay for detecting the porcine circovirus type 2 specific antibodies is a modified indirect porcine circovirus (PCV) type 2-based and recombinant capsid protein (ORF2)-based ELISA for the detection of antibodies to PCV.

* * * * *